US011802289B2

(12) United States Patent
Ferraro et al.

(10) Patent No.: US 11,802,289 B2
(45) Date of Patent: Oct. 31, 2023

(54) TRANSIENT SILENCING OF ARGONAUTE1 AND ARGONAUTE4 TO INCREASE RECOMBINANT PROTEIN EXPRESSION IN PLANTS

(71) Applicant: PlantForm Corporation, Toronto (CA)

(72) Inventors: Kiva Ferraro, Guelph (CA); Michael Marit, Guelph (CA); Michael D. McLean, Guelph (CA)

(73) Assignee: PlantForm Corporation, Toronto (CA)

( * ) Notice: Subject to any disclaimer, the term of this patent is extended or adjusted under 35 U.S.C. 154(b) by 14 days.

(21) Appl. No.: 16/635,402

(22) PCT Filed: Aug. 2, 2018

(86) PCT No.: PCT/CA2018/050949
§ 371 (c)(1),
(2) Date: Jan. 30, 2020

(87) PCT Pub. No.: WO2019/023806
PCT Pub. Date: Feb. 7, 2019

(65) Prior Publication Data
US 2020/0362359 A1 Nov. 19, 2020

Related U.S. Application Data

(60) Provisional application No. 62/540,696, filed on Aug. 3, 2017.

(51) Int. Cl.
*C12N 15/82* (2006.01)
*C07K 16/32* (2006.01)

(52) U.S. Cl.
CPC .......... *C12N 15/8218* (2013.01); *C07K 16/32* (2013.01); *C12N 15/8258* (2013.01); *C07K 2317/13* (2013.01); *C07K 2317/24* (2013.01)

(58) Field of Classification Search
None
See application file for complete search history.

(56) References Cited

U.S. PATENT DOCUMENTS

| 8,715,963 B2 * | 5/2014 | Sethuraman | A61P 31/14 435/336 |
| 2008/0092252 A1 | 4/2008 | Cammue et al. | |
| 2011/0296556 A1 * | 12/2011 | Sammons | C12N 15/8207 435/410 |

FOREIGN PATENT DOCUMENTS

| WO | 2007/033436 A1 | 3/2007 |
| WO | 2011/112570 A1 | 9/2011 |
| WO | 2014/043786 A1 | 3/2014 |
| WO | 2014/195011 A1 | 12/2014 |
| WO | 2015/168733 A1 | 11/2015 |

OTHER PUBLICATIONS

GenBank Accession DQ321489, dated Jun. 8, 2006. (Year: 2006).*
Circelli, et al. (Bioengineered bugs 1.3 (2010): 221-224). (Year: 2010).*
Danielson et al. (FEBS letters 587.8 (2013): 1198-1205). (Year: 2013).*
Jones, et al. (Plantphysiology 141.2 (2006): 598-606). (Year: 2006).*
Wielopolska, et al. (Plant Biotechnology Journal 3.6 (2005): 583-590). (Year: 2006).*
Carbonell, Alberto, ed. Plant Argonaute Proteins: Methods and Protocols. Humana Press, 2017. "Plant ARGONAUTEs: Features, Functions, and Unknowns", p. 11). (Year: 2017).*
Helliwell et al. (Methods in Enzymology 30.4 (2003): 289-295). (Year: 2003).*
Vezina et al., "Transient co-expression for fast and high-yield production of antibodies with human-like N-glycans in plants" Plant Biotechnol. J., 2009, vol. 7, pp. 442-455.
Jones et al., "Virus-induced gene silencing of Argonaute genes in Nicotiana benthamiana demonstrates that extensive systemic silencing requires Argonaute1-like and Argonaute4-like genes" Plant Physiol. 141:598-606. Jun. 2006 (Jun. 2006). ISSN: 0032-0889.
Danielson et al., "Studying the RNA silencing pathway with the p19 protein" FEBS Lett 587:1198-1205. Jan. 2013 (Jan. 2013). ISSN: 0014-5793.
Choi et al., "Improvement of N-glycan site occupancy of therapeutic glycoproteins produced in Pichia pastoris" Appl. Microbiol. Biotechnol. 95:671-682. May 2012 (May 2012). ISSN: 0185-7598.
Bustos-Sanmamed et al., "A Medicago truncatula rdr6 allele impairs transgene silencing and endogenous phased siRNA production but not development" Plant Biotechnol J. Dec. 2014; 12(9): 1308-18. doi: 10.1111/pbi. 12230.
Parent et al., "Respective contributions of *Arabidopsis* DCL2 and DCL4 to RNA silencing" The Plant Journal, Jan. 2015; 81(2), pp. 223-232. doi: 10.1111/tpj.12720.
Liu et al., (2012). "Validation of reference genes for gene expression studies in virus-infected Nicotiana benthamiana using quantitative real-time PCR". PLoS One, 7(9), e46451, pp. 1-14.
Scholthof et al., (2011). "Identification of an ARGONAUTE for antiviral RNA silencing in Nicotiana benthamiana". Plant physiology, 156(3), pp. 1548-1555.
Varallyay, E. et al., "Plant virus-mediated induction of miR168 is associated with repression of ARGONAUTE1 accumulation", The EMBO Journal (2010); vol. 29, No. 20; pp. 3507-3519.
Database Embase [Online] Elsevier Science Publishers, Amsterdam, NL; Oct. 1, 2012 (Oct. 1, 2012), Wu et al.: "Nicotiana benthamiana isotig00178.Nb_seed_capmRNA sequence", Database accession No. KA758652.
The Supplementary European Search Report issued in connection to corresponding EP application No. 18842376.8 dated Mar. 12, 2021.

* cited by examiner

*Primary Examiner* — Charles Logsdon
(74) *Attorney, Agent, or Firm* — Bereskin & Parr LLP/S.E.N.C.R.L., s.r.l.; Ainslie Parsons

(57) ABSTRACT

A plant or plant cell with reduced endogenous AGO1 and AGO4 expression compared to a wild-type plant or plant cell is provided. In one embodiment, the plant or plant cell further comprises a nucleic acid sequence encoding a recombinant protein and the plant or plant cell has increased expression of the recombinant protein compared to a wild-type plant or plant cell comprising the nucleic acid sequence. Methods of reducing aglycosylation of recombinant protein produced in plants are also provided.

11 Claims, 20 Drawing Sheets

Specification includes a Sequence Listing.

TRANSIENT SILENCING OF ARGONAUTE1 AND ARGONAUTE4 TO INCREASE RECOMBINANT PROTEIN EXPRESSION IN PLANTS

CROSS-REFERENCE TO RELATED APPLICATIONS

This disclosure is a national phase entry of PCT/CA2018/050949 filed Aug. 2, 2018 (which designates the U.S.), which claims the benefit of U.S. provisional application No. 62/540,696 filed Aug. 3, 2017, the contents of which are incorporated herein by reference in its entirety.

INCORPORATION OF SEQUENCE LISTING

A computer readable form of the Sequence Listing "20436-P52491US01_SequenceListing.txt" (12,288 bytes), submitted via EFS-WEB and created on Jan. 30, 2020, is herein incorporated by reference.

FIELD

The present disclosure relates to a host plant or plant cell for recombinant protein production wherein the plant or cell has reduced expression of endogenous ARGONAUTE1 (AGO1) and ARGONAUTE4 (AGO4). The disclosure also relates to methods of increasing recombinant protein production in plants. The disclosure further relates to methods of reducing aglycosylation of recombinant protein produced in plants.

BACKGROUND

ARGONAUTE (AGO) proteins play a central role in the RNA-induced silencing complex (RISC), which is responsible for post-transcriptional gene silencing (PTGS) through RNA interference (RNAi). Suppression of RNAi has been demonstrated to improve transient recombinant protein expression. Co-expression of the Tomato bushy stunt virus (TBSV) protein P19 is currently a benchmark standard for suppression of RNAi in Nicotiana benthamiana for improving transiently expressed recombinant protein yields. While P19 is reasonably well tolerated by N. benthamiana, the protein induces a hypersensitive response of varying severity. In other Nicotiana species, such as N. tabacum, this response extends to visible leaf necrosis, thereby limiting the potential hosts that can be used for recombinant protein expression (Angel et al., 2011, Garabagi et al., 2012). This is significant as N. tabacum, produces greater biomass than N. benthamiana, and therefore may be a more cost-effective host. Recent studies characterizing several N. benthamiana AGOs indicated that some members of this family can be silenced via T-DNA hairpins without negatively affecting plant health (Jones et al., 2006, Scholthof et al., 2011).

In common with other recombinant expression systems, such as Chinese Hamster Ovary (CHO) or Yeast (Pichia pastoris, Saccharomyces cerevisiae), glycoproteins expressed in plants may show less than 100% occupancy at the normal N-linkage sites (Rademacher et al., 2008, Vamvaka et al., 2016). For monoclonal antibody products, the extent of aglycosylation is normally in the range 10-20% of heavy chains having no N-linked glycan. Several approaches have been made to overcome this heterogeneity, in CHO cells by increasing dolichol content or by adopting specific glucose-feeding regimes in the bioreactor, amongst other strategies. In yeast systems, it has been found that expression of a protist (eg Leishmania or Toxoplasma) single-subunit oligosaccharyl transferase (OST, the enzyme responsible for transfer of the sugar chain to the nascent polypeptide during secretion) can significantly increase glycan site occupancy.

A need remains for host plants with improved recombinant protein production and/or host plants which produce recombinant protein with reduced aglycosylation levels.

SUMMARY

The present disclosure describes an N. benthamiana plant with reduced expression of AGO1 and AGO4. This plant shows increased production of recombinant proteins. The present disclosure also shows that expressing Leishmania STT3D under the control of the Cauliflower mosaic virus (CaMV) 35S promoter or Arabidopsis thaliana ACT2 (AtACT2) promoter in an N. benthamiana plant with suppressed expression of AGO1 and AGO4 reduces aglycosylation of protein produced by the plant. Expressing LmSTT3D behind the AtACT2 promoter (but not the 35S promoter) in an N. benthamiana plant co-expressing P19 protein from Tomato Bushy Stunt Virus (TBSV) is shown to also reduce the aglycosylation of protein produced by the plant.

Accordingly, the disclosure provides a plant or plant cell with reduced endogenous AGO1 and AGO4 expression compared to a wild-type plant or plant cell.

In one embodiment, the endogenous expression of AGO1 and AGO4 is reduced transiently.

In another embodiment, endogenous expression of AGO1 and AGO4 is reduced using RNA interference.

In another embodiment, the plant or plant cell expresses at least two short hairpin RNA (shRNA), wherein a first shRNA targets AGO1 and a second shRNA targets AGO4.

In one embodiment, the first shRNA comprises
(a) a nucleic acid molecule comprising SEQ ID NO: 5 or a fragment thereof, a sequence having at least 75%, 80%, 85%, 90%, 95% or 99% sequence identity to SEQ ID NO: 5 or a fragment thereof; or the complement thereof.

In another embodiment, the second shRNA comprises
(a) a nucleic acid molecule comprising SEQ ID NO: 6 or a fragment thereof, a sequence having at least 75%, 80%, 85%, 90%, 95% or 99% sequence identity to SEQ ID NO: 6 or a fragment thereof; or the complement thereof, or
(b) a nucleic acid molecule comprising SEQ ID NO: 7 or a fragment thereof, a sequence having at least 75%, 80%, 85%, 90%, 95% or 99% sequence identity to SEQ ID NO: 7 or a fragment thereof; or the complement thereof In another embodiment, the first shRNA comprises a nucleic acid molecule comprising SEQ ID NO: 5 or a fragment thereof, a sequence having at least 75%, 80%, 85%, 90%, 95% or 99% sequence identity to SEQ ID NO: 5 or a fragment thereof; or the complement thereof,
the second shRNA comprises a nucleic acid molecule comprising SEQ ID NO: 6 or a fragment thereof, a sequence having at least 75%, 80%, 85%, 90%, 95% or 99% sequence identity to SEQ ID NO: 6 or a fragment thereof; or the complement thereof,
and the plant or plant cell further expresses a third shRNA, wherein the third shRNA comprises a nucleic acid molecule comprising SEQ ID NO: 7 or a fragment thereof, a sequence having at least 75%, 80%, 85%, 90%, 95% or 99% sequence identity to SEQ ID NO: 7 or a fragment thereof; or the complement thereof.

In another embodiment, multiple AGO1 and/or AGO4 genes have reduced expression compared to a wild-type plant or plant cell.

In another embodiment, the plant or plant cell is a tobacco plant or plant cell, optionally a *Nicotiana* plant or plant cell.

In another embodiment, the plant or plant cell is a *Nicotiana* plant or plant cell and has reduced AGO1-1 and AGO1-2 expression compared to a wild-type plant or plant cell.

In another embodiment, the plant or plant cell is a *Nicotiana* plant or plant cell and has reduced AGO4-1 and AGO4-2 expression compared to a wild-type plant or plant cell.

In another embodiment, the plant or plant cell expresses a nucleic acid molecule encoding the P19 protein from Tomato Bushy Stunt Virus (TBSV).

In another embodiment, the plant or plant cell expresses a nucleic acid molecule encoding the STT3D protein from *Leishmania*.

In another embodiment, expression of the nucleic acid molecule encoding the STT3D protein is driven by the CaMV 35S or AtACT2 promoter.

In another embodiment, the plant or plant cell further comprises a nucleic acid sequence encoding a recombinant protein.

In another embodiment, the plant or plant cell has increased expression of the recombinant protein compared to a wild-type plant or plant cell comprising the nucleic acid sequence.

In another embodiment, the recombinant protein is an antibody or fragment thereof.

In another embodiment, the antibody or fragment thereof is trastuzumab, or ranibizumab.

In another embodiment, the recombinant protein is a serum protein or a therapeutic enzyme.

In another embodiment, the therapeutic enzyme is butyrylcholinesterase.

In another embodiment, the recombinant protein is a vaccine or a Virus Like Particle.

In another embodiment, the vaccine or Virus Like Particle is for Porcine Epidemic Diarrhea Virus (PEDv).

The disclosure also provides an isolated nucleic acid molecule comprising:
(a) SEQ ID NO: 5, a sequence having at least 75%, 80%, 85%, 90%, 95% or 99% sequence identity to SEQ ID NO: 5 or the complement thereof
(b) SEQ ID NO: 6, a sequence having at least 75%, 80%, 85%, 90%, 95% or 99% sequence identity to SEQ ID NO: 6 or the complement thereof, or
(c) SEQ ID NO: 7, a sequence having at least 75%, 80%, 85%, 90%, 95% or 99% sequence identity to SEQ ID NO: 7 or the complement thereof.

In one embodiment, the nucleic acid molecule is comprised in a vector.

The disclosure also provides a ribonucleic acid (RNA) molecule encoded by the nucleic acid molecule.

In one embodiment, the molecule is a double-stranded ribonucleic acid (dsRNA) molecule.

In another embodiment, the dsRNA molecule is a short hairpin RNA (shRNA) molecule.

The disclosure also provides a method of enhancing the production of a recombinant protein in a plant or plant cell comprising: (a) introducing and expressing a nucleic acid molecule encoding a recombinant protein in a plant or plant cell with reduced endogenous AGO1 and AGO4 expression compared to a wild-type plant or plant cell; and (b) growing the plant or plant cell to obtain a plant or plant cell that expresses the recombinant protein.

The disclosure further provides a method of enhancing the production of a recombinant protein in a plant or plant cell comprising:
(a) introducing and expressing
(i) the nucleic acid molecule described above and
(ii) a nucleic acid molecule encoding a recombinant protein
in the plant or plant cell
(b) growing the plant or plant cell to obtain a plant or plant cell that expresses the recombinant protein.

In one embodiment, the recombinant protein is an antibody or fragment thereof.

In another embodiment, the antibody or fragment thereof is trastuzumab, or ranibizumab.

In another embodiment, the recombinant protein is a serum protein or a therapeutic enzyme.

In another embodiment, the therapeutic enzyme is butyrylcholinesterase.

In another embodiment, the recombinant protein is a vaccine or a Virus Like Particle.

In another embodiment, the vaccine or Vaccine Like Particle is for Porcine Epidemic Diarrhea Virus (PEDv).

The disclosure also provides a method of reducing the aglycosylated fraction of a recombinant protein produced in a plant or plant cell comprising:
(a) introducing and expressing (i) a nucleic acid molecule encoding the STT3D protein from *Leishmania* and (ii) a nucleic acid molecule encoding a recombinant protein, in a plant or plant cell with reduced endogenous AGO1 and AGO4 expression compared to a wild-type plant or plant cell; and
(b) growing the plant or plant cell to obtain a plant or plant cell that expresses the recombinant protein.

In one embodiment, expression of the nucleic acid molecule encoding the STT3D protein is driven by the CaMV 35S or AtACT2 promoter.

In another embodiment, the recombinant protein has reduced aglycosylation compared to a control plant or plant cell that does not comprise a nucleic acid molecule encoding the STT3D protein from *Leishmania*.

The disclosure also provides a genetically modified plant or plant cell expressing (i) a nucleic acid molecule encoding the P19 protein from Tomato Bushy Stunt Virus (TBSV) and (ii) a nucleic acid molecule encoding the STT3D protein from *Leishmania*, wherein expression of the nucleic acid molecule encoding the STT3D protein is driven by a weak or medium strength promoter.

In one embodiment, the weak or medium strength promoter is *Arabidopsis thaliana* ACT2.

In another embodiment, plant or plant cell is a tobacco plant or plant cell, optionally a *Nicotiana* plant or plant cell.

In another embodiment, the plant or plant cell further comprises a nucleic acid sequence encoding a recombinant protein.

In another embodiment, the plant or plant cell has increased expression of the recombinant protein compared to a wild-type plant or plant cell comprising the nucleic acid sequence.

In another embodiment, the recombinant protein is an antibody or fragment thereof.

In another embodiment, the antibody or fragment thereof is trastuzumab, or ranibizumab.

In another embodiment, the recombinant protein is a serum protein or a therapeutic enzyme.

In another embodiment, the therapeutic enzyme is butyrylcholinesterase.

In another embodiment, the recombinant protein is a vaccine or Virus Like Particle.

In another embodiment, the vaccine or Virus like Particle is for Porcine Epidemic Diarrhea Virus (PEDv).

The disclosure also provides a method of reducing the aglycosylated fraction of a recombinant protein produced in a plant or plant cell comprising:

(a) introducing a nucleic acid molecule encoding a recombinant protein into the plant or plant cell plant or plant cell expressing (i) a nucleic acid molecule encoding the P19 protein from Tomato Bushy Stunt Virus (TBSV) and (ii) a nucleic acid molecule encoding the STT3D protein from *Leishmania*, wherein expression of the nucleic acid molecule encoding the STT3D protein is driven by a weak or medium strength promoter; and (b) growing the plant or plant cell to obtain a plant or plant cell that expresses the recombinant protein.

In one embodiment, the recombinant protein has reduced aglycosylation compared to a control plant or plant cell that does not comprise a nucleic acid molecule encoding *Leishmania* STT3D.

The disclosure also provides a protein produced by a plant or plant cell as described herein, or by a method as described herein.

Other features and advantages of the present disclosure will become apparent from the following detailed description. It should be understood, however, that the detailed description and the specific Example while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION

Figure 1:
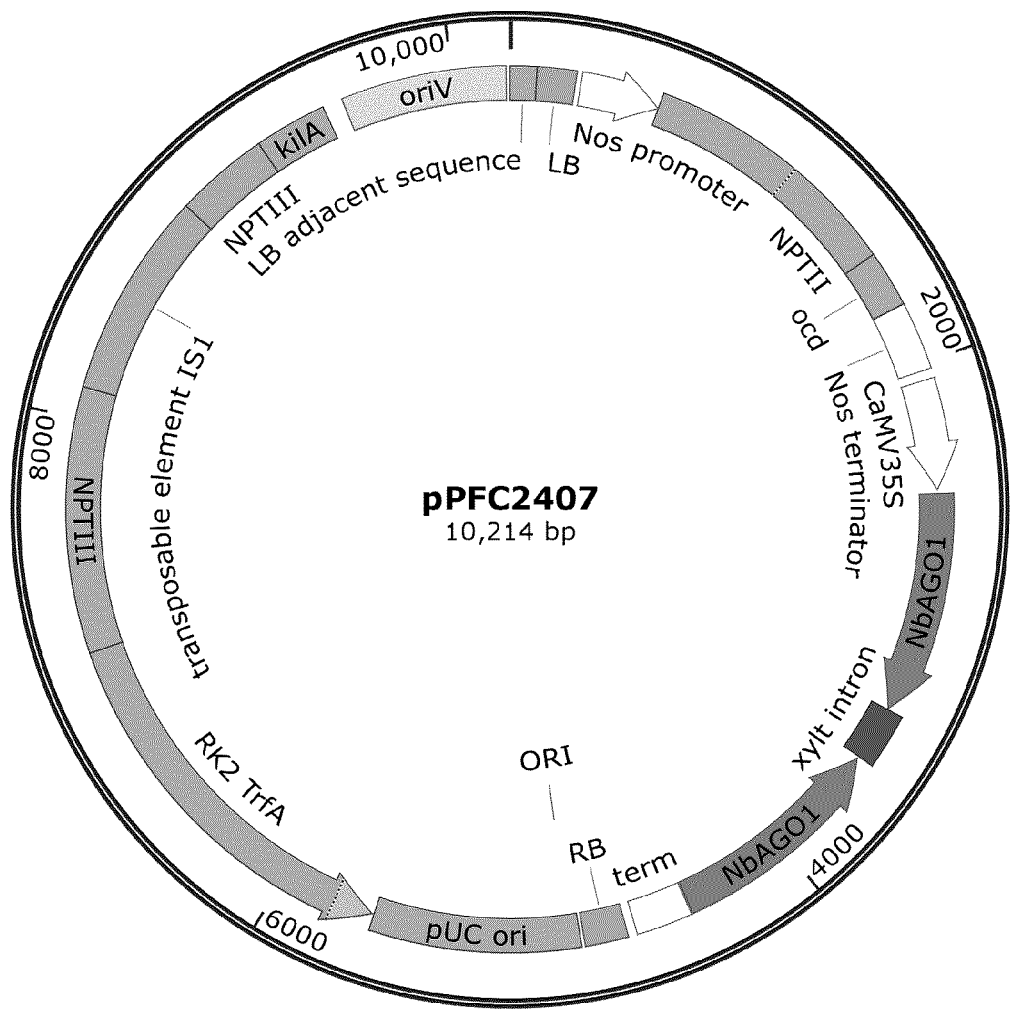
FIG. 1 shows a NbAGO1 silencing vector (pPFC2407). Hairpin is composed of two 849-bp repeat fragments (labelled "NbAGO1") and a 210-bp intron sequence (labelled "xylt intron") from *Arabidopsis thaliana* beta-1,2-xylosyltransferase (TAIR AGI #AT5G55500).

The present inventors have shown that suppression of AGO1 and AGO4 expression in plants increases recombinant protein expression.

The present inventors have also shown that expressing Leishmania STT3D (LmSTT3D) can reduce the aglycosylation of protein produced by the plants, however this effect is dependent on both a) the method used for post-transcriptional gene silencing (PTGS) and b) the promoter used to control expression of LmSTT3D. In particular, expressing LmSTT3D under control of the CaMV 35S or AtACT2 promoter in plants with suppressed expression of AGO1 and AGO4 reduces the fraction of protein produced by the plants which is aglycosylated. Expressing LmSTT3D under control of the AtACT2 promoter (but not the CaMV 35S promoter) in plants co-expressing P19 protein from Tomato Bushy Stunt Virus (TBSV) also reduces aglycosylation of protein produced by the plants.

Compositions of Matter

Plants and Plant Cells

Accordingly, the disclosure provides a genetically modified plant, or plant cell with reduced endogenous AGO1 and AGO4 expression compared to a wild-type plant or plant cell.

ARGONAUTE (AGO) proteins are a conserved family of proteins which play a key role in the RNA-induced silencing complex (RISC). RISC is responsible for gene expression silencing through RNA interference (RNAi).

The term "AGO1" as used herein refers to the gene which encodes ARGONAUTE1 protein (Ago1). The term "AGO1" includes AGO1 from any species or source. The term also includes sequences that have been modified from any of the known published sequences of AGO genes or proteins. The AGO1 gene or protein may have any of the known published sequences for AGO1 which can be obtained from public sources such as GenBank. The N. benthamiana genome encodes two AGO1 genes, termed "AGO1-1" and "AGO1-2" (also referred to as AGO1a and AGO1b, respectively). Examples of the N. benthamiana sequences for AGO1-1 and AGO1-2 include Accession Nos. KR942296, DQ321488 and DQ321489. The aforementioned sequences are incorporated herein by reference.

The term "AGO4" as used herein refers to the gene which encodes ARGONAUTE4 protein (Ago4). The term "AGO4" includes AGO4 from any species or source. The term also includes sequences that have been modified from any of the known published sequences of AGO4 genes or proteins. The AGO4 gene or protein may have any of the known published sequences for AGO4 which can be obtained from public sources such as GenBank. The N. benthamiana genome encodes two AGO4 genes, termed "AGO4-1" and "AGO4-2" (also referred to as AGO4a and AGO4b, respectively). Examples of the N. benthamiana sequences for AGO4-1 and AGO4-2 include Accession Nos. DQ321490 and DQ321491. The aforementioned sequences are incorporated herein by reference.

As used herein, the term AGO1 expression includes both AGO1 gene expression and Ago1 protein expression. Likewise, the term AGO4 expression includes both AGO4 gene expression and Ago4 protein expression.

Endogenous AGO1 and AGO4 expression can be reduced by any method known in the art. In one embodiment, an AGO1 and/or AGO4 inhibitor is used to reduce endogenous AGO1 and AGO4 expression. The term "inhibitor" refers to an agent that reduces, decreases or otherwise blocks expression or activity of its target and includes any substance that is capable of inhibiting the expression or activity of the target and includes, without limitation, small molecules, antisense oligonucleotide molecules (antisense nucleic acid molecules), siRNAs or shRNAs, aptamers, proteins, antibodies (and fragments thereof), gene editing agents and other substances directed at the target expression or activity.

The term "siRNA" refers to a short inhibitory RNA (often 21-24 bp fragments) that can be used to silence gene expression of a specific gene. The siRNA can be a short RNA hairpin (e.g. shRNA) that activates a cellular degradation pathway directed at mRNAs corresponding to the siRNA. Methods of designing specific siRNA molecules or shRNA molecules are known to a person of skill in the art. It is known in the art that efficient silencing is obtained with siRNA duplex complexes paired to have a two nucleotide 3' overhang. Adding two thymidine nucleotides is thought to add nuclease resistance. A person skilled in the art will recognize that other nucleotides can be added.

Endogenous AGO1 and AGO4 expression can be reduced transiently (for example, with the use of siRNA) or permanently (for example, by introducing gene mutations or deletions into the germline).

In one specific embodiment of the present disclosure, endogenous AGO1 and AGO4 expression is reduced through the use of siRNA targeting genes encoding AGO1 and AGO4, respectively.

An siRNA molecule can be referred to as being "directed to" or "targeted to" the gene to be silenced (for example, AGO1 or AGO4). The terms "silence," "inhibit the expression of," "down-regulate the expression of," "suppress the expression of" and the like in as far as they refer to a target gene, herein refer to the at least partial suppression of the expression of the target gene.

RNA interference techniques involve transformation using RNAi plasmid constructs (Helliwell and Waterhouse, 2005). Such plasmids (also referred to herein as vectors) are composed of the target gene or a fragment of the target gene to be silenced. The RNAi construct driven by a suitable promoter, for example, the Cauliflower mosaic virus (CaMV) 35S promoter, is integrated into the plant genome at an insertion locus (also referred to herein as a T-DNA (transfer DNA) insertion locus) and subsequent transcription of the transgene leads to an RNA molecule that folds back on itself to form a double-stranded hairpin RNA (hpRNA). This double-stranded RNA structure (also referred to herein as a short hairpin RNA (shRNA) is recognized by the plant and cut into siRNAs. siRNAs associate with a protein complex (RISC) which goes on to direct degradation of the mRNA for the target gene.

As used herein, the term "wild-type" refers to a plant or plant cell which is not genetically modified. Optionally, a wild-type plant or plant cell has normal (non-modified), endogenous expression levels of AGO1 and AGO4 genes or proteins.

In one embodiment of the present disclosure, endogenous AGO1 expression is reduced by at least 5%, 10%, 25%, 50%, 75% or 100% compared to a wild-type plant or plant cell. In another embodiment, the plant or plant cell has no detectable endogenous AGO1 expression.

In another embodiment, endogenous AGO4 expression is reduced by at least 5%, 10%, 25%, 50%, 75% or 100% compared to a wild-type plant or plant cell. In another embodiment, the plant or plant cell has no detectable endogenous AGO4 expression.

The plant or plant cell may be any plant or plant cell, including, without limitation, tobacco plants or plant cells, tomato plants or plant cells, maize plants or plant cells, alfalfa plants or plant cells, a *Nicotiana* species such as *Nicotiana benthamiana* or *Nicotiana tabacum*, rice plants or plant cells, *Lemna major* or *Lemna minor* (duckweeds), safflower plants or plant cells or any other plants or plant cells that are both agriculturally propagated and amenable to genetic modification for the expression of recombinant or foreign proteins.

In a specific embodiment of the present disclosure, the plant or plant cell is a tobacco plant. In another embodiment, the plant is a *Nicotiana* plant or plant cell, and more specifically a *Nicotiana benthamiana* or *Nicotiana tabacum* plant or plant cell. In another embodiment, the plant is an RNAi-based glycomodified plant. In a more specific embodiment the plant exhibits RNAi-induced gene-silencing of endogenous fucosyltransferase (FT) and xylosyltransferase (XT) genes. In another embodiment, the plant or plant cell is a KDFX plant or plant cell. In yet another embodiment, the plant or plant cell is a ΔXT/FT plant (as published in Strasser et al., 2008). In yet another embodiment, the plant or plant cell is an *N. benthamiana* plant which has been mutagenized such that neither the FT and XT genes, nor the proteins encoded by the FT or XT genes are functional. For example, mutagenesis-based point mutations can result in early stop codons and therefore no protein expression, or true knock-outs (for example, those obtained using the CRISPR methodology) in which the promotor or coding region is excised and therefore there is no transcript produced.

As used herein, the phrase "RNAi-based glycomodified plant" means a plant that expresses polypeptides with altered glycan profiles, wherein the altered profiles result from the use of interfering RNA (RNAi) gene-silencing technology. Plant-specific sugar residues on the N-glycan core, namely core α1,3-fucose and β1,2-xylose, are immunogenic in mammals (Bardor et al., 2003; Jin et al., 2008). Because of the existence of multiple endogenous FT and XT genes in most plants, modified glycosylation patterns are preferably created with the use of RNAi technology (Cox et al., 2006; Sourrouille et al., 2008; Strasser et al., 2008).

As used herein, the term "plant" includes a plant cell and a plant part. The term "plant part" refers to any part of a plant including but not limited to the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like.

As used herein, the term "nucleic acid molecule" means a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present disclosure may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

Figure 4:
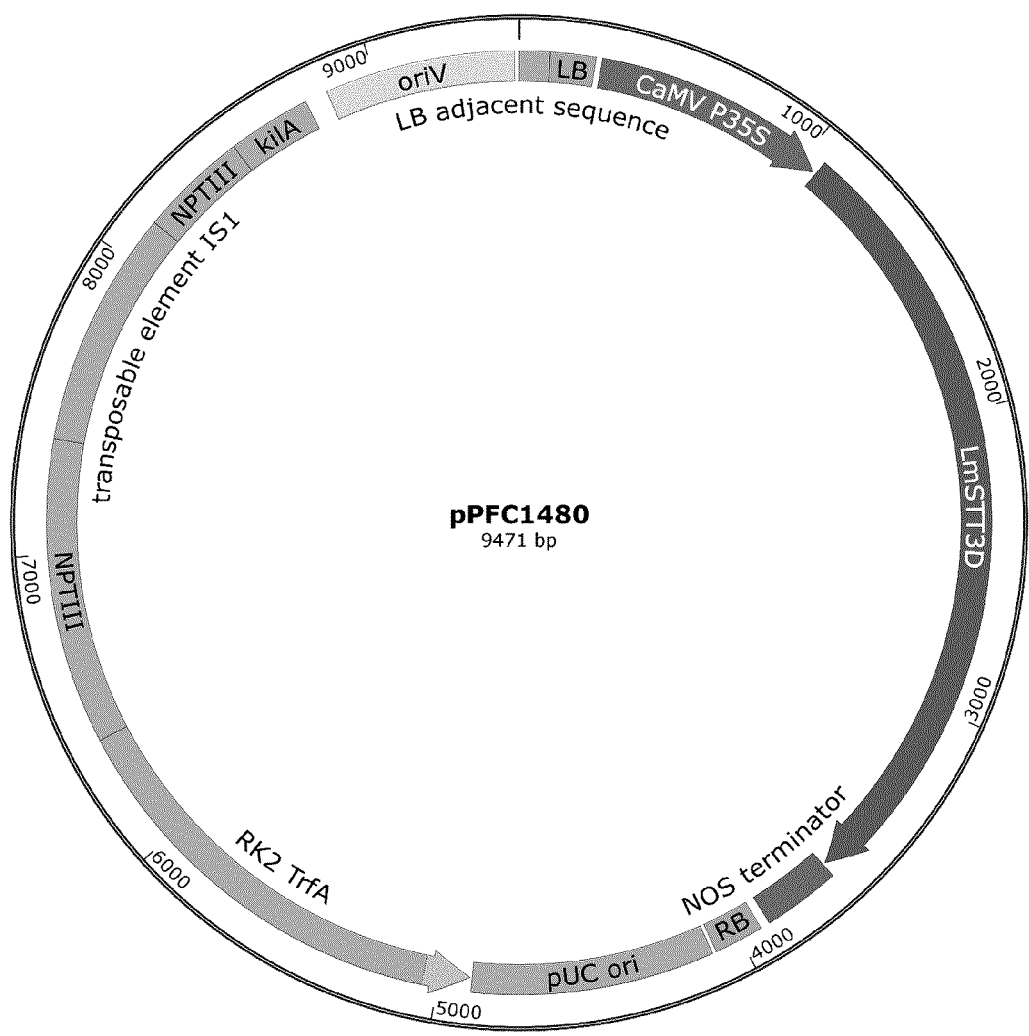
FIG. 4 shows a *Leishmania major* STT3D expression vector (pPFC1480).
Figure 5:
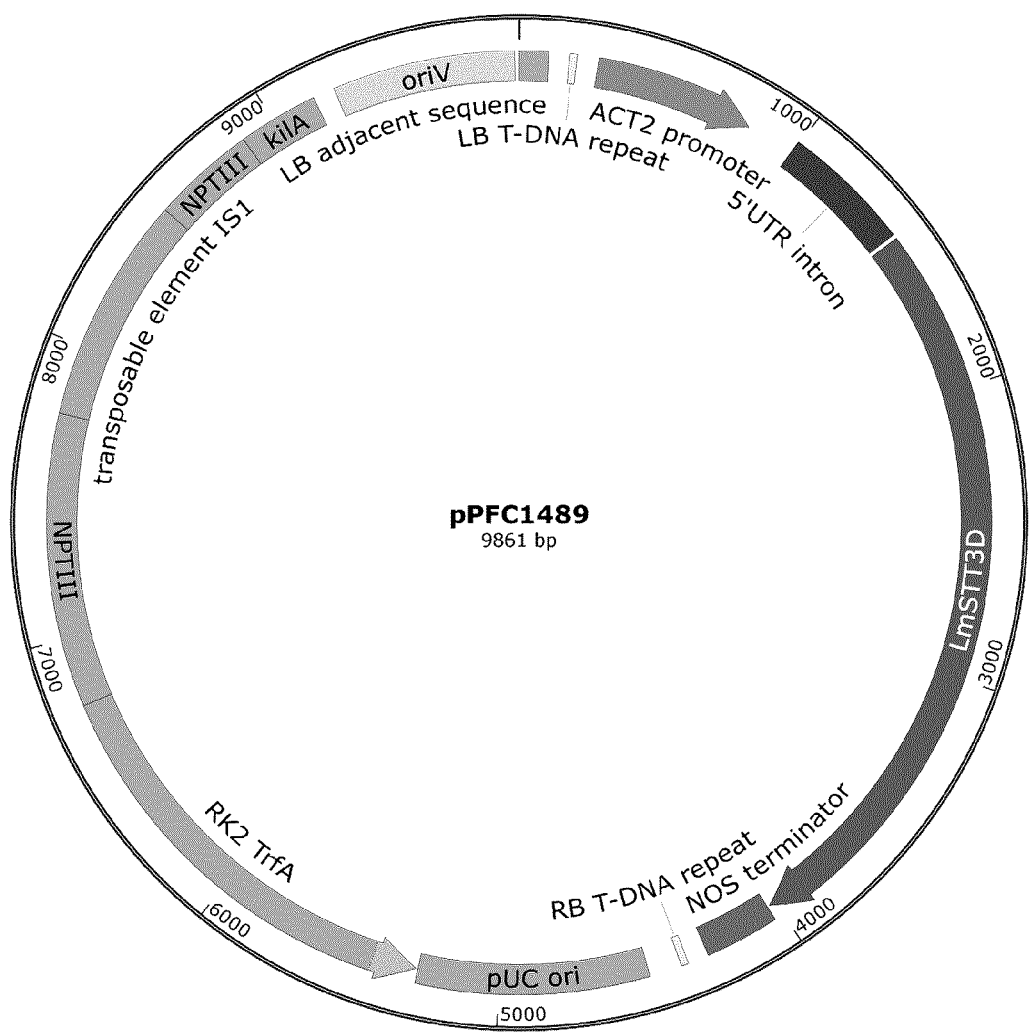
FIG. 5 shows a *Leishmania major* STT3D expression vector (pPFC1489).

As used herein, the term "vector" or "expression vector" means a nucleic acid molecule, such as a plasmid, comprising regulatory elements and a site for introducing transgenic DNA, which is used to introduce said transgenic DNA into a plant or plant cell. Regulatory elements include promoters, 5' and 3' untranslated regions (UTRs) and terminator sequences or truncations thereof. The regulatory elements of the vector can be selected from the 35S promoter and 5'UTR of the Cauliflower Mosaic Virus (CaMV; Genbank accession: AF140604) or the *Arabidopsis thaliana* actin2 promoter (AtACT2; Genbank accession U41998). The AtACT2 promoter is approximately 1.2 kb long and contains a 442 bp intron sequence, encoded in the mRNA leader beginning at the −10 position, which is required for strong expression by the promoter (An et al., 1996, An and Meagher, 2010). A detailed description of the structure of and elements within the AtACT2 promoter can be found in the papers by An et al., (1996) and An and Meagher (2010). Constitutive promoter strength is dependent on a number of variables, including species and tissue type. In *Arabidopsis*, the AtACT2 promoter has been described as stronger than the common CaMV 35S promoter with duplicated enhancer elements (An et al., 2010). But in *N. benthamiana* leaves, using the vectors described herein (pPFC1480 vs pPFC1489; FIG. 4-5), $P_{AtACT2}$ gene expression is lower than that by the double enhanced $P_{35S}$.

As used herein, the term "weak or medium strength promoter" means a promoter that results in lower gene expression in a particular species and/or tissue type compared with another promoter, for example a promoter known to be strong promoter in that species and/or tissue type.

The transgenic DNA can comprise a target gene or a fragment of the target gene to be silenced via siRNA. As used herein, the term "silencing vector" or "silencing plasmid" refers to a single, operably linked set of regulatory elements that includes a promoter (for example, CaMV $P_{35S}$), a sense sequence of the target gene and an antisense sequence of the target gene. Examples of silencing vectors in the present disclosure include pPFC2407 (NbAGO1 silencing vector), pPFC2408 (NbAGO4 silencing vector) and pPFC2419 (NbAGO4 silencing vector).

In further embodiments, the transgenic DNA can encode a recombinant protein, which can be expressed in and isolated from a plant or plant cell.

As used herein, the term "recombinant protein" means any polypeptide that can be expressed in a plant cell, wherein said polypeptide is encoded by transgenic DNA introduced into the plant cell via use of an expression vector.

In one embodiment, the recombinant protein is an antibody or antibody fragment. In a specific embodiment, the antibody is trastuzumab or a modified form thereof, consisting of 2 heavy chains (HC) and 2 light chains (LC). Trastuzumab (Herceptin® Genentech Inc., San Francisco, Calif.) is a humanized murine immunoglobulin $G1_\kappa$ antibody that is used in the treatment of metastatic breast cancer.

In another embodiment, the antibody fragment is ranibizumab (trade name Lucentis®). In another embodiment, the recombinant protein is an enzyme such as a therapeutic enzyme. In a specific embodiment, the therapeutic enzyme is butyrylcholinesterase. Butyrylcholinesterase (also known as pseudocholinesterase, plasma cholinesterase, BCHE, or BuChE) is a non-specific cholinesterase enzyme that hydrolyses many different choline esters. In humans, it is found primarily in the liver and is encoded by the BCHE gene. It is being developed as an antidote to nerve-gas poisoning.

In yet another embodiment, the recombinant protein is a vaccine or a Virus-Like Particle (VLP) (for example, a VLP based on the M (membrane) protein of the Porcine Epidemic Diarrhea (PED) virus). In another embodiment, the VLP comprises both the M and E proteins of the virus. The nucleic acid molecules encoding the M and E proteins can be incorporated separately into one expression vector each or incorporated together into a single expression vector comprising multiple expression cassettes.

The nucleic acid molecules encoding the HC and LC of an antibody or antibody fragment can also be incorporated separately into one expression vector each or incorporated together into a single expression vector comprising multiple expression cassettes.

As used herein, the term "expression cassette" means a single, operably linked set of regulatory elements that includes a promoter, a 5' UTR, an insertion site for transgenic DNA, a 3' UTR and a terminator sequence.

As used herein, the term "antibody fragment" includes, without limitation, Fab, Fab', F(ab')$_2$, scFv, dsFv, ds-scFv, dimers, minibodies, diabodies, and multimers thereof and bispecific antibody fragments.

In one embodiment, a signal peptide that directs the polypeptide to the secretory pathway of plant cells may be placed at the amino termini of recombinant proteins, including antibody HCs and/or LCs. In a specific embodiment, a peptide derived from *Arabidopsis thaliana* basic chitinase signal peptide (SP), namely MAKTNLFLFLIFSLLLSLSSA (SEQ ID NO:1), is placed at the amino- (N-) termini of both the HC and LC (Samac et al., 1990).

In another embodiment, the native human butyrylcholinesterase signal peptide (SP), namely MHSKVTIICIRFLFW-FLLLCMLIGKSHT (SEQ ID NO:2), is placed at the amino- (N-) termini of a therapeutic enzyme such as butyrylcholinesterase (GenBank: AAA99296.1).

Other signal peptides can be mined from GenBank [http://www.ncbi.nlm.nih.gov/genbank/] or other such databases, and their sequences added to the N-termini of the HC or LC, nucleotides sequences for these being optimized for plant preferred codons as described above and then synthesized. The functionality of a SP sequence can be predicted using online freeware such as the SignalP program [http://www.cbs.dtu.dk/services/SignalP/].

In a specific embodiment, the nucleic acid constructs encoding recombinant proteins, including antibody HCs and/or LCs, and therapeutic proteins such as enzymes, are optimized for plant codon usage. In particular, the nucleic acid sequence encoding the heavy chain and light chain can be modified to incorporate preferred plant codons. In a specific embodiment, coding sequences for both the HC and LC, including the SP in both cases, were optimized for expression in *Nicotiana* species.

In another embodiment, the plant or plant cell expresses the STT3D protein from *Leishmania major* (LmSTT3D; GenBank XP_003722509). In one embodiment, the STT3D protein from *Leishmania major* is expressed from a nucleic acid molecule which has been modified to optimize expression levels in tobacco plants. In a specific embodiment, the modified LmSTT3D-encoding nucleic acid molecule has the sequence shown in SEQ ID NO:3.

The STT3D protein can be expressed from an expression vector comprising a single expression cassette or from an expression vector containing one or more additional cassettes, wherein the one or more additional cassettes comprise transgenic DNA encoding one or more recombinant proteins. Examples of STT3D expression vectors include pPFC1480 and pPFC1489.

In one embodiment, the plant or plant cell expresses the P19 protein from Tomato Bushy Stunt Virus (TBSV; Genbank accession: M21958). In a preferred embodiment, the P19 protein from TBSV is expressed from a nucleic acid molecule which has been modified to optimize expression levels in *Nicotiana* plants. In a specific embodiment, the modified P19-encoding nucleic acid molecule has the sequence shown in SEQ ID NO:4.

Figure 6:
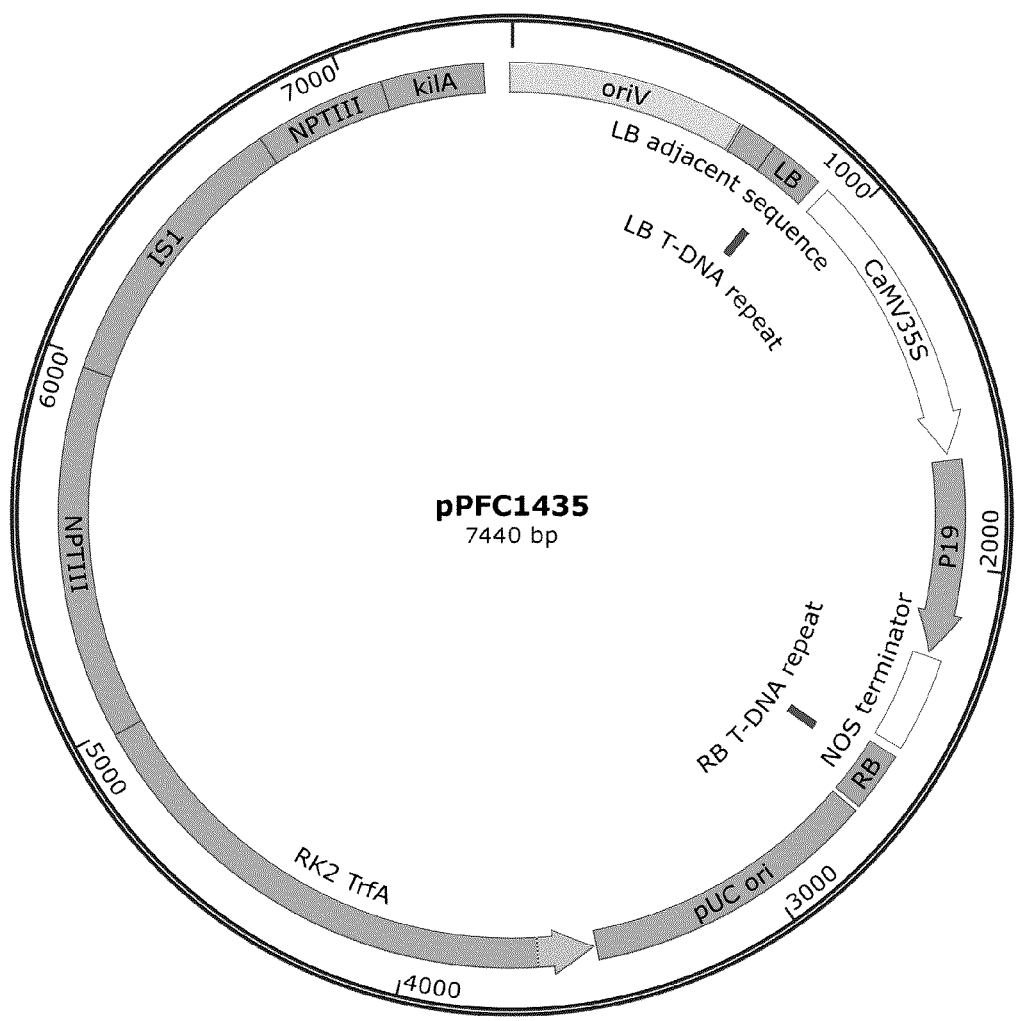
FIG. 6 shows a Tomato Bushy Stunt Virus P19 expression vector (pPFC1435).
Figure 7:
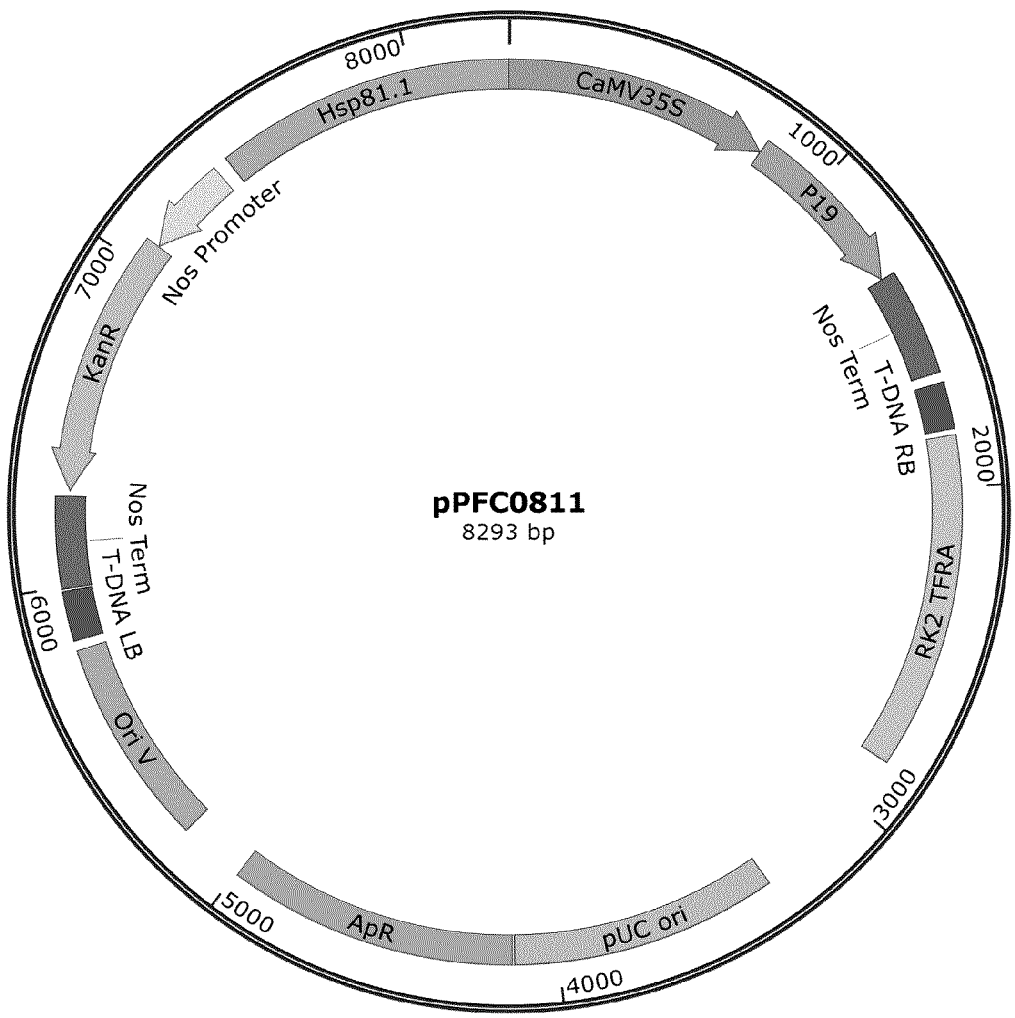
FIG. 7 shows a Tomato Bushy Stunt Virus P19 expression vector (pPFC0811).

The P19 protein can be expressed from an expression vector comprising a single expression cassette or from an expression vector containing one or more additional cassettes, wherein the one or more additional cassettes comprise transgenic DNA encoding one or more recombinant proteins or RNA-interference inducing hairpins. Examples of P19 expression vectors include pPFC1435 (FIG. 6) and pPFC0811 (FIG. 7).

Nucleic Acids and Vectors

Also provided herein are nucleic acid molecules (for example, dsRNA, siRNA, miRNA and shRNA) that inhibit expression of AGO1 and/or AGO4.

In one embodiment, the nucleic acid molecule comprises, consists of, or consists essentially of a fragment of least 10, 20, 30, 40, 50, 60, 80 or 100 contiguous nucleic acids of AGO1 or AGO4, or a sequence having at least 75%, 80%, 85%, 90%, 95% or 99% sequence identity to a fragment of least 10, 20, 30, 40, 50, 60, 80 or 100 contiguous nucleic acids of AGO1 or AGO4. In another embodiment, the nucleic acid molecule comprises, consists of, or consists essentially of a fragment of least 10, 20, 30, 40, 50, 60, 80 or 100 contiguous nucleic acids of AGO1 or AGO4, or a sequence having at least 75%, 80%, 85%, 90%, 95% or 99% sequence identity to a fragment of least 10, 20, 30, 40, 50, 60, 80 or 100 contiguous nucleic acids of AGO1 or AGO4.

In another embodiment, the nucleic acid molecule comprises, consists of, or consists essentially of a polynucleotide having at least 75%, 80%, 85%, 90%, 95% or 99% sequence identity to SEQ ID NO: 5, SEQ ID NO: 6 or SEQ ID NO: 7 or the complement thereof. In another embodiment, the nucleic acid molecule comprises, consists of, or consists essentially of a polynucleotide having at least 75%, 80%, 85%, 90%, 95% or 99% sequence identity to a fragment of SEQ ID NO: 5, SEQ ID NO: 6 or SEQ ID NO: 7 or the complement thereof.

In another embodiment, the nucleic acid molecule comprises, consists of, or consists essentially of SEQ ID NO: 5, SEQ ID NO: 6 or SEQ ID NO: 7 or the complement thereof. In another embodiment, the nucleic acid molecule comprises, consists of, or consists essentially of a fragment of SEQ ID NO: 5, SEQ ID NO: 6 or SEQ ID NO: 7 or the complement thereof.

As used herein, the expression "a fragment of SEQ ID NO: 5, SEQ ID NO: 6 or SEQ ID NO: 7" refers to a fragment corresponding to at least 10, 20, 30, 40, 50, 60, 80 or 100 contiguous nucleic acids of SEQ ID NO: 5, SEQ ID NO: 6 or SEQ ID NO: 7.

Also provided herein is a ribonucleic acid (RNA) molecule encoded by the nucleic acid molecule. In one embodiment, the RNA molecule is a double-stranded ribonucleic acid (dsRNA) molecule. In another embodiment, the dsRNA molecule is a shRNA (short hairpin RNA) molecule.

Various vectors and vector systems for expressing the nucleic acid molecules and proteins described herein are contemplated. Examples of vector systems useful in the methods of the present disclosure include, but are not limited to, the Magnifection (Icon Genetics), pEAQ (Lomonosoff), Geminivirus (Arizona State U.), and vivoXPRESS® vector systems.

In one embodiment, a vector is provided comprising a nucleic acid molecule as described herein operably linked to promoter, for example the 35S promoter of the Cauliflower Mosaic Virus or the *Arabidopsis thaliana* actin2 promoter.

In one embodiment, the vector comprises a nucleic acid molecule as described herein and the complement thereof. Expression of both the nucleic acid molecule and its complement forms an shRNA.

As used here, the term "sequence identity" refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions multiplied by 100%). In one embodiment, the two sequences are the same length. The determination of percent identity between two sequences can also be accomplished using a mathematical algorithm. One non-limiting example of a mathematical algorithm utilized for the comparison of two sequences is the algorithm of Karlin and Altschul (1990), modified as in Karlin and Altschul (1993). Such an algorithm is incorporated into the NBLAST and XBLAST programs of Altschul et al. (1990). BLAST nucleotide searches can be performed with the NBLAST nucleotide program parameters set, e.g., for score=100, wordlength=12 to obtain nucleotide sequences homologous to a nucleic acid molecules of the present disclosure. BLAST protein searches can be performed with the XBLAST program parameters set, e.g., to score-50, wordlength=3 to obtain amino acid sequences homologous to a protein molecule of the present disclosure. To obtain gapped alignments for comparison purposes, Gapped BLAST can be utilized as described in Altschul et al. (1997). Alternatively, PSI-BLAST can be used to perform an iterated search which detects distant relationships between molecules (Altschul et al., 1997). When utilizing BLAST, Gapped BLAST, and PSI-Blast programs, the default parameters of the respective programs (e.g., of XBLAST and NBLAST) can be used (see, e.g., the NCBI website). Another non-limiting example of a mathematical algorithm utilized for the comparison of sequences is the algorithm of Myers and Miller (1988). Such an algorithm is incorporated in the ALIGN program (version 2.0) which is part of the Genetics Computer Group (GCG) sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

The sequences of the present disclosure may be at least 75%, 80%, 85%, 90%, 95% or 99% identical to the sequences set out within. Importantly, the substantially identical sequences retain the activity and specificity of the reference sequence.

Methods

The inventors have demonstrated that they can achieve high levels of expression of recombinant proteins in *N. benthamiana* by reducing the endogenous expression of AGO1 and AGO4. The inventors have also demonstrated that expressing LmSTT3D under control of the CaMV 35S or AtACT2 promoter in plants with suppressed expression of AGO1 and AGO4 reduces the aglycosylation of protein produced by the plants. Expressing LmSTT3D under control of the AtACT2 promoter (but not the CaMV 35S promoter) in plants co-expressing P19 protein from Tomato Bushy Stunt Virus (TBSV) also reduces the aglycosylation of protein produced by the plants.

Accordingly, the present disclosure provides a method of enhancing the production of a recombinant protein in a plant or plant cell comprising:

(a) introducing a nucleic acid molecule encoding a recombinant protein into a plant or plant cell with reduced endogenous AGO1 and AGO4 expression compared to a wild-type plant or plant cell; and (b) growing the plant or plant cell to obtain a plant or plant cell that expresses the recombinant protein.

In one embodiment, the plant or plant cell expresses at least 5%, 10%, 25%, 50%, 75% or 100% more recombinant protein than a control plant or plant cell without reduced endogenous AGO1 and AGO4 expression.

In one embodiment, the recombinant protein is the only heterologous protein expressed in the plant or plant cell. In another embodiment, the recombinant protein is co-expressed with the P19 protein from TBSV and/or the STT3D protein from *Leishmania*. The P19 protein, STT3D protein and expression vectors for expressing them are described above.

The disclosure also provides a method of reducing the fraction of protein produced in a plant or plant cell which is aglycosylated in a plant or plant cell comprising:

(a) introducing (i) a nucleic acid molecule encoding the STT3D protein from *Leishmania* and (ii) a nucleic acid molecule encoding a recombinant protein, into a plant or plant cell with reduced endogenous AGO1 and AGO4 expression compared to a wild-type plant or plant cell; and (b) growing the plant or plant cell to obtain a plant or plant cell that expresses the recombinant protein.

In one embodiment, expression of the nucleic acid molecule encoding the STT3D protein is driven by the CaMV 35S or AtACT2 promoter.

In another embodiment, the recombinant protein expressed by the plant cell has at least 5%, 10%, 25%, 50%, 75% or 100% less aglycosylation, or the fraction of recombinant protein which is aglycosylated is reduced by 5%, 10%, 25%, 50%, 75% or 100% compared to recombinant protein expressed from a control plant or plant cell, for example a plant or plant cell that does not express the STT3D protein from *Leishmania*.

The disclosure further provides a method of reducing the aglycosylated content of recombinant protein in produced in a plant or plant cell comprising:

(a) introducing a nucleic acid molecule encoding a recombinant protein into the plant or plant cell plant or plant cell expressing (i) a nucleic acid molecule encoding the P19 protein from Tomato Bushy Stunt Virus (TBSV) and (ii) a nucleic acid molecule encoding the STT3D protein from *Leishmania*, wherein expression of the nucleic acid molecule encoding the STT3D protein is driven by a weak or medium strength promoter; and (b) growing the plant or plant cell to obtain a plant or plant cell that expresses the recombinant protein.

In one embodiment, the promoter is an AtACT2 promoter.

In another embodiment, the recombinant protein expressed by the plant cell has at least 5%, 10%, 25%, 50%, 75% or 100% less aglycosylation or the fraction of recombinant protein which is aglycosylated is reduced by 5%, 10%, 25%, 50%, 75% or 100% compared to recombinant protein expressed from a control plant or plant cell, for example a plant or plant cell that does not express the STT3D protein from *Leishmania*.

In one embodiment, the recombinant protein is an antibody or antibody fragment, comprising a heavy chain variable region and a light chain variable region. In a specific embodiment, the antibody is trastuzumab. In another specific embodiment, the antibody fragment is ranibizumab.

In another specific embodiment, the recombinant protein is an enzyme such as butyrylcholinesterase.

In another specific embodiment, the recombinant protein is a vaccine or Vaccine Like Particle for Porcine Epidemic Diarrhea virus.

In one embodiment, the nucleic acid molecule encoding the heavy chain variable region and the nucleic acid molecule encoding the light chain variable region may be introduced into the plant cell on separate expression vectors. In another embodiment, the nucleic acid molecule encoding the heavy chain variable region and the nucleic acid molecule encoding the light chain variable region may be introduced into the plant cell on the same expression vector. In such an embodiment, the heavy chain and the light chain would be expressed separately and then combine in the plant cell in order to prepare the desired antibody or antibody fragment.

The phrase "introducing" a nucleic acid molecule or an expression vector into a plant or plant cell includes both the stable integration of the recombinant nucleic acid molecule into the genome of a plant cell to prepare a transgenic plant as well as the transient integration of the recombinant nucleic acid into a plant or part thereof.

The nucleic acid molecules and expression vectors may be introduced into the plant cell using techniques known in the art including, without limitation, electroporation, an accelerated particle delivery method, a cell fusion method or by any other method to deliver the expression vectors to a plant cell, including *Agrobacterium* mediated delivery, or other bacterial delivery such as *Rhizobium* sp. NGR234, *Sinorhizobium meliloti* and *Mesorhizobium loti* (Chung et al, 2006).

The plant cell may be any plant cell, including, without limitation, tobacco plants, tomato plants, maize plants, alfalfa plants, *Nicotiana benthamiana, Nicotiana tabacum, Nicotiana tabacum* of the cultivar cv. Little Crittenden, rice plants, *Lemna major* or *Lemna minor* (duckweeds), safflower plants or any other plants that are both agriculturally propagated and amenable to genetic modification for the expression of recombinant or foreign proteins.

In one embodiment, the recombinant protein is expressed transiently, with or without P19, and with or without STT3D, in *N. benthamiana*.

In one embodiment, the recombinant protein (and optionally P19 and/or STT3D) are expressed in an RNAi-based glycomodified plant. In a specific embodiment, the plant is an *N. benthamiana* plant. In a more specific embodiment the *N. benthamiana* plant exhibits RNAi-induced gene-silencing of endogenous fucosyltransferase (FT) and xylosyltransferase (XT) genes. In another embodiment, the plant or plant cell is a KDFX plant or plant cell. In another embodiment, the plant or plant cell is a ΔXT/FT plant (as published in Strasser et al., 2008). In yet another embodiment, the plant or plant cell is an *N. benthamiana* plant which has been mutagenized so as to have complete knockouts of all FT and XT genes.

The phrase "growing a plant or plant cell to obtain a plant that expresses a recombinant protein" includes both growing transgenic plant cells into a mature plant as well as growing or culturing a mature plant that has received the nucleic acid molecules encoding the recombinant protein. One of skill in the art can readily determine the appropriate growth conditions in each case.

In a specific embodiment, expression vectors containing the recombinant nucleic acid molecules are introduced into

*Agrobacterium tumefaciens* by electroporation procedures. The *N. benthamiana* plants can be vacuum infiltrated according to the protocol described by Marillonnet et al. (2005) and Giritch et al. (2006) with several modifications. Briefly, all cultures can be grown at 28° C. and 220 rpm to a final optical density at 600 nm ($OD_{600}$) of 1.8. Equal volumes are combined and pelleted by centrifugation at 8,000 rpm for 4 minutes, resuspended and diluted by 10 in infiltration buffer (10 mM 1-(N-morpholino)ethanesulphonic acid (MES) pH 5.5, 10 mM $MgSO_4$). Alternatively, each of the 5 *Agrobacterium* cultures could be grown to lower OD values and Beer's Law could be applied to determine the volumes of each culture required to make a bacterial suspension cocktail whereby the concentrations of each bacterial strain were equivalent. Alternatively, lower or higher concentrations of expression vectors could be used to optimize the expression of recombinant protein. Alternatively, higher or lower dilutions with infiltration buffer could be used.

The aerial parts of four to five-week-old *N. benthamiana* plants are submerged in a chamber containing the *A. tumefaciens* resuspension solution, after which a vacuum (0.5 to 0.9 bar) is applied for 90 seconds followed by a slow release of the vacuum, after which plants were returned to the greenhouse for 7 days before being harvested. Alternatively, longer or shorter periods under vacuum, and/or vacuum release, could be used. Alternatively, longer or shorter periods of growth in greenhouse could be used. Alternatively, standard horticultural improvement of growth, maximized for recombinant protein production could be used (see Colgan et al., 2010).

Alternately, instead of transient introduction of expression vectors containing the HC and LC coding sequences of an antibody, or the coding sequence of a therapeutic enzyme, stable transgenic plants could be made using one vector on which the nucleic acid molecule encoding the heavy chain variable region and the nucleic acid molecule encoding the light chain variable region may be introduced together in the same construct. In one embodiment, the nucleic acid molecule encoding the heavy chain variable region may be attached to the nucleic acid molecule encoding the light chain variable region by a linker in order to prepare a single chain variable region fragment (scFv).

In another embodiment, the nucleic acid molecule encoding the heavy chain and the nucleic acid molecule encoding the light chain may be introduced into the plant cell on separate expression vector nucleic acid constructs. In such an embodiment, the heavy chain and the light chain would be expressed from separate transgenic loci and then combine in the plant cell in order to prepare the antibody or antibody fragment.

Expression vector(s) containing antibody HC and LC genes would be introduced into *A. tumefaciens* EHA105 or other suitable *Agrobacterium* isolates or other suitable bacterial species capable of introducing DNA to plants for transformation such as *Rhizobium* sp., *Sinorhizobium meliloti, Mesorhizobium loti* and other species (Broothaerts et al. 2005; Chung et al., 2006), by electroporation or other bacterial transformation procedures. *Agrobacterium* clones containing expression vectors would be propagated on Luria-Bertani (LB) plates containing rifampicin (30 mg/l) and kanamycin (50 mg/l), or other selectable media, depending on the nature of the selectable marker genes on the vector. *Agrobacterium*-mediated leaf disk transformation (Horsch et al., 1985; Gelvin, 2003), or similar protocols involving wounded tobacco (*N. tabacum*, variety 81V9 or tissue of other tobacco varieties such as are listed in Conley et al., 2011) or *N. benthamiana* or other plant species such as those of the Solanaceae, maize, safflower, *Lemna* spp., etc. would be infected with the *Agrobacterium* culture (diluted as appropriate, for example to OD600=0.6) and plated on Murashige and Skoog plus vitamins medium (MS; Sigma), supplemented with agar (5.8%; Sigma) and containing kanamycin (100 mg/L) or 500 cefotaxime (mg/L) or other selectable media, depending on the nature of the selectable marker genes on the expression vector, for selection of transformed plant cells. Production of shoots would be induced with naphthalene acetic acid (NAA; 0.1 mg/L; Sigma) and benzyl adenine (BA; 1 mg/L; Sigma) in the medium. For induction of roots, the newly formed shoots were moved to Magenta boxes (Sigma-Aldrich, Oakville, ON) on MS medium (as above) that was lacking NAA and BA. After roots are formed, plants would be transplanted to soil and could be raised in greenhouse culture. For plant transformation, as many as possible or at least 25 primary transgenic plants would be produced. ELISA and quantitative immunoblots would be performed on each plant to characterize levels of total and active antibody produced by the plants, respectively (Almquist et al., 2004; 2006; McLean et al., 2007; Olea-Popelka et al., 2005; Makvandi-Nejad et al., 2005).

After selection of antibody-expressing primary transgenic plants, or concurrent with selection of antibody-expressing plants, derivation of homozygous stable transgenic plant lines can be performed. Primary transgenic plants are grown to maturity, allowed to self-pollinate, and produce seed. Homozygosity can be verified by the observation of 100% resistance of seedlings on kanamycin plates (50 mg/L), or other selectable drug as indicated above. A homozygous line with single T-DNA insertions, that are shown by molecular analysis to produce most amounts of antibody, can be chosen for breeding to homozygosity and seed production, ensuring subsequent sources of seed for homogeneous production of antibody by the stable transgenic or genetically modified crop (Olea-Popelka et al., 2005; McLean et al., 2007; Yu et al., 2008).

Alternatively, the expression vector with both HC and LC genes, or 2 expression vectors (one with a HC gene and the other with a LC gene), could be used to transiently infect a plant or plant tissues, as described above, and tissue harvested as described above for subsequent purification of antibody.

The antibody or antibody fragment or the enzyme may be purified or isolated from the plants using techniques known in the art, including homogenization, clarification of homogenate and affinity purification. Homogenization is any process that crushes or breaks up plant tissues and cells and produces homogeneous liquids from plant tissues, such as using a blender, or juicer, or grinder, or pulverizer such as mortar and pestle, etc. Clarification involves either/and/or centrifugation, filtration, etc. Affinity purification uses Protein A or Protein G or Protein L or antibodies that bind antibodies; affinity purification for enzymes uses ligands that bind them, such as procainamide or huprine (for Butyryl Cholinesterase).

The following non-limiting Examples are illustrative of the present disclosure:

Example 1

Transient Silencing of Native ARGONAUTE1 and ARGONAUTE4 to Increase Recombinant Protein Expression in *Nicotiana benthamiana*

AGO-RNAi

Figure 2:
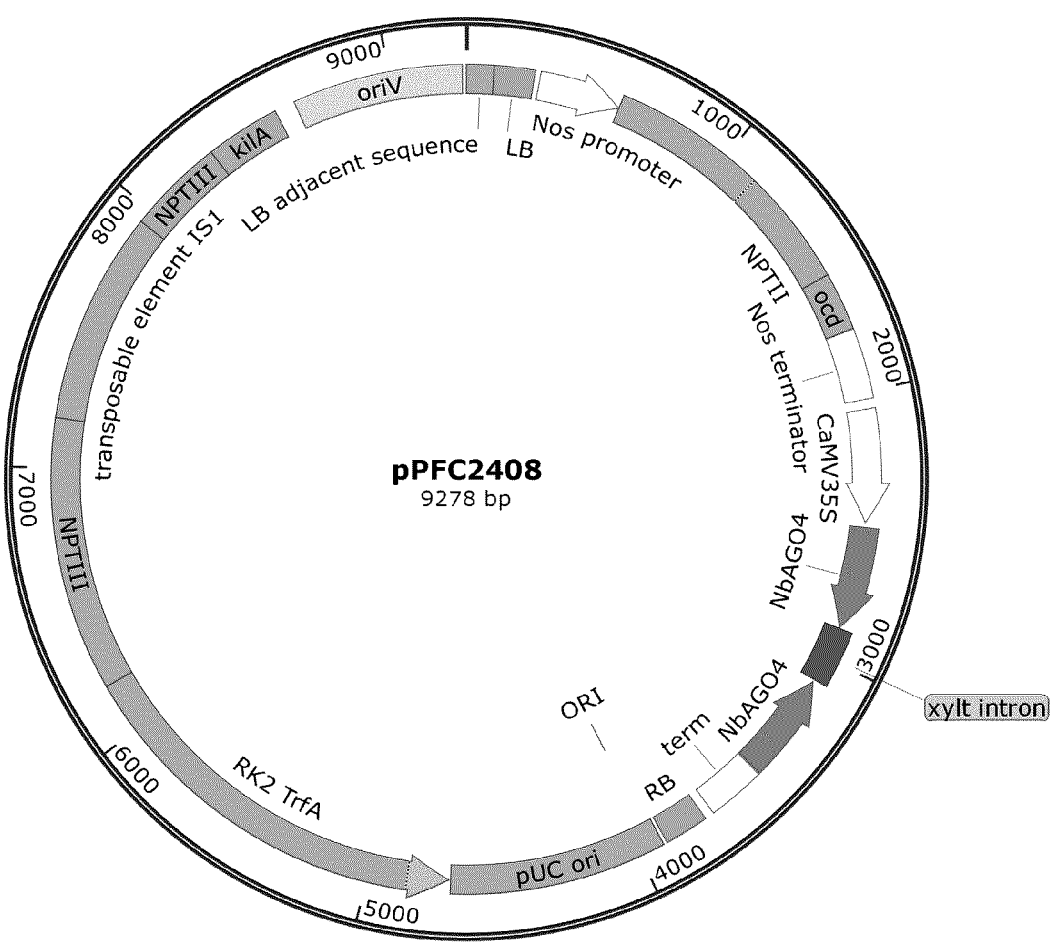
FIG. 2 shows a NbAGO4 silencing vector (pPFC2408). Hairpin is composed of two 380-bp repeat fragments (labelled "NbAGO4") and a 210-bp intron sequence (labelled "xylt intron") from *Arabidopsis thaliana* beta-1,2-xylosyltransferase (TAIR AGI #AT5G55500).
Figure 3:
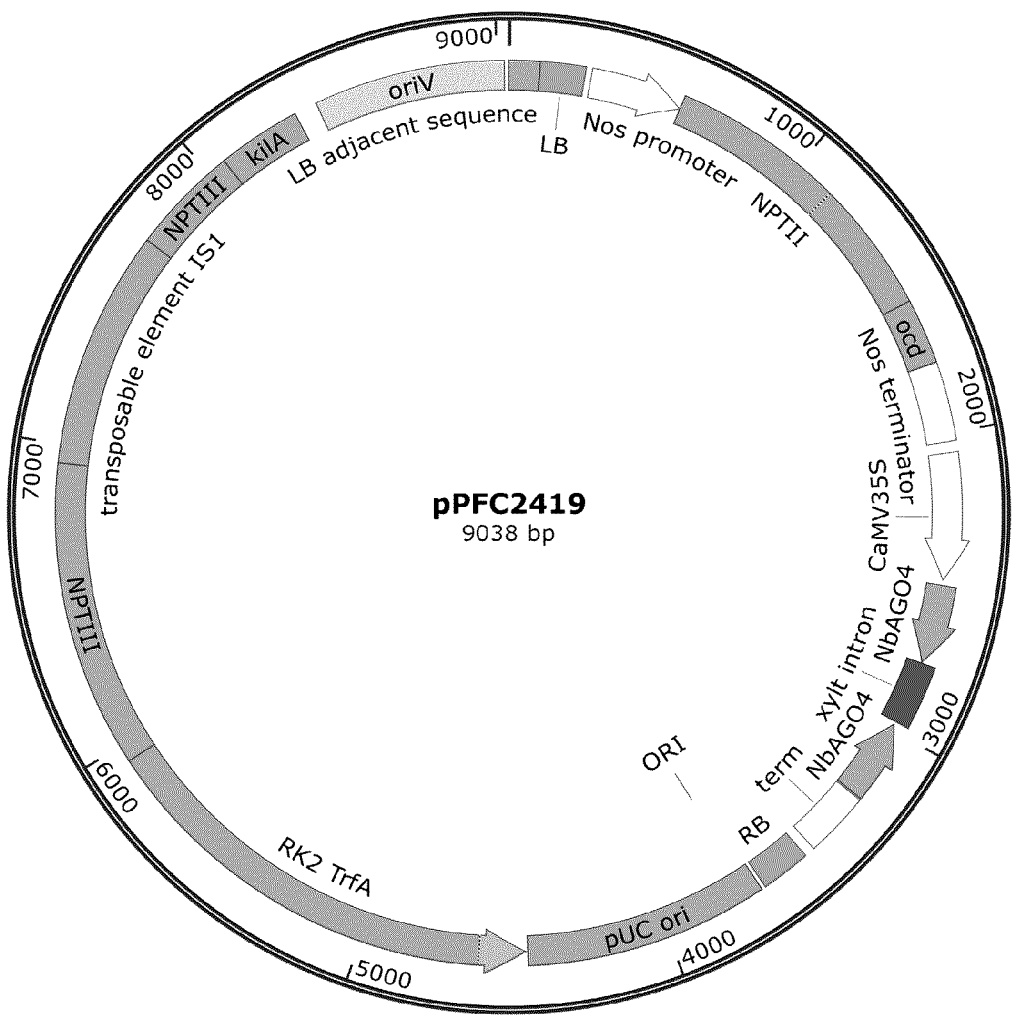
FIG. 3 shows a NbAGO4 silencing vector (pPFC2419). Hairpin is composed of two 260-bp repeat fragments (labelled "NbAGO4") and a 210-bp intron sequence (labelled "xylt intron") from *Arabidopsis thaliana* beta-1,2-xylosyltransferase (TAIR AGI #AT5G55500).
Figure 8:
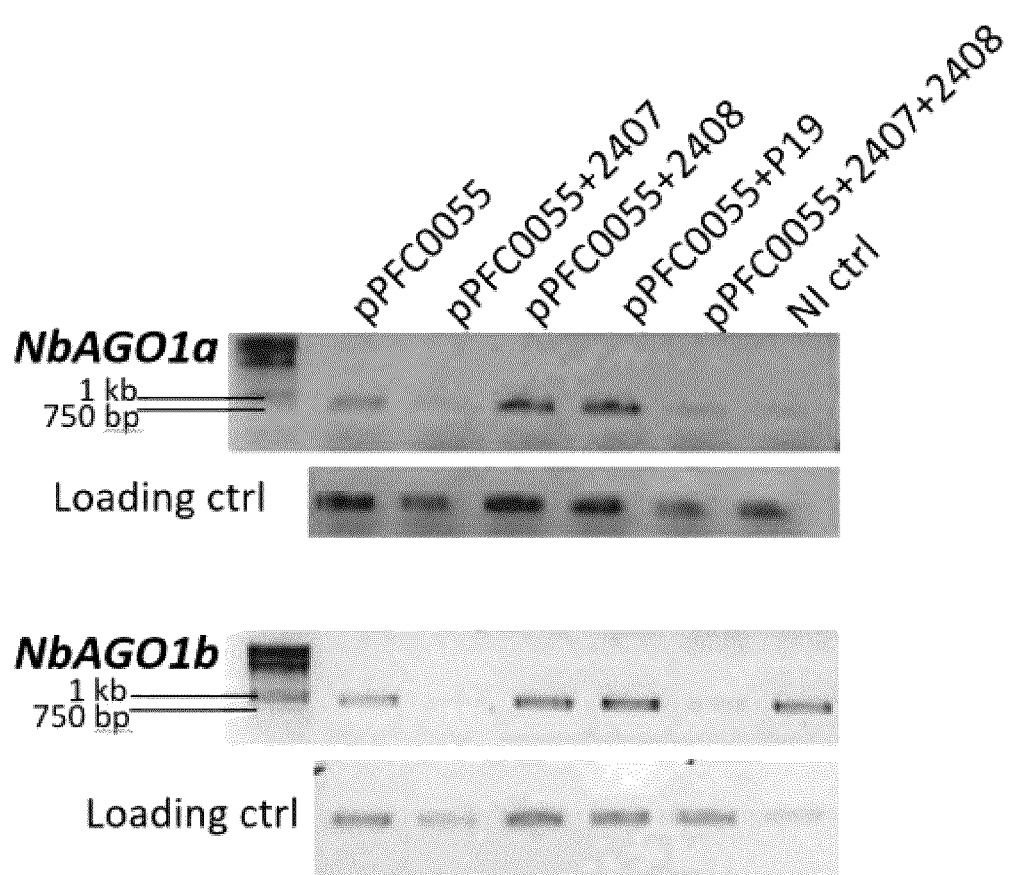
FIG. 8 shows semi-quantitative reverse transcription-PCR detection of NbAGO1 transcripts using cDNA from leaves spot infiltrated with pPFC0055, pPFC2407, pPFC2408, and pPFC0811 (P19). pPFC0055, trastuzumab heavy and light chain expression vector. 60S ribosomal protein gene L23 used as loading control (Liu et al., 2012). 30 cycles of PCR performed. Nl ctrl, non-infiltrated control.
Figure 9:
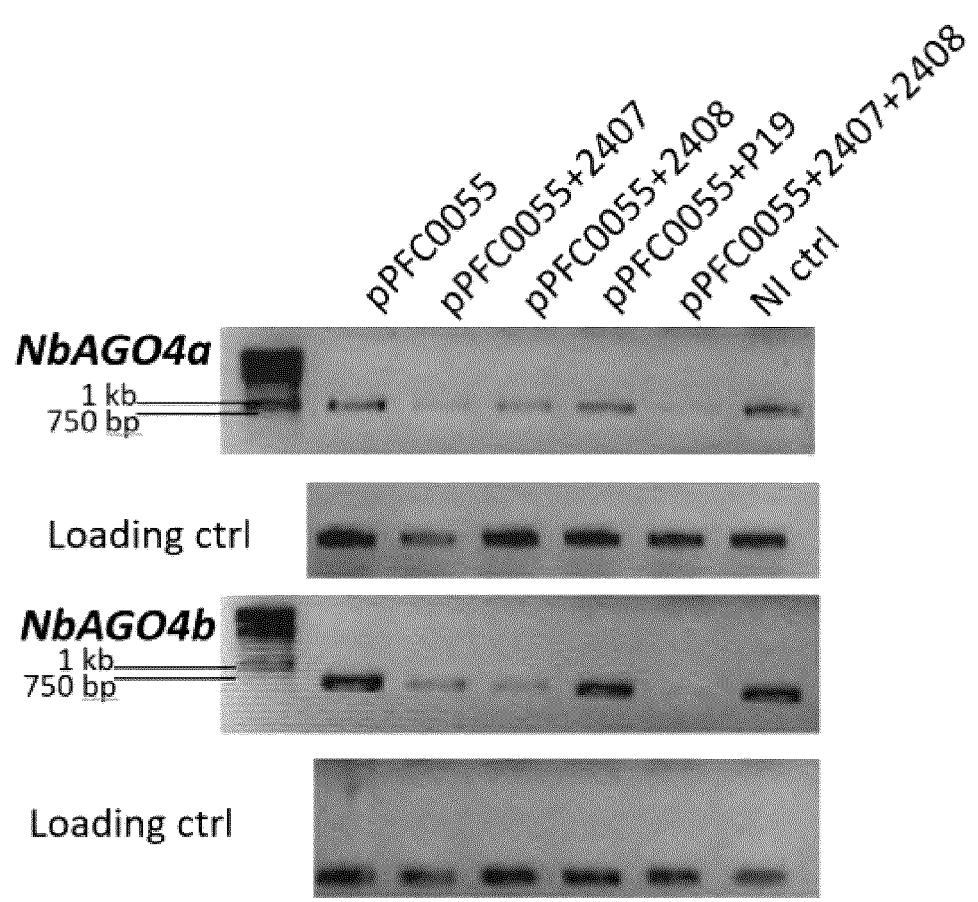
FIG. 9 shows semi-quantitative reverse transcription-PCR detection of NbAGO4 transcripts using cDNA from leaves spot infiltrated with pPFC0055, pPFC2407, pPFC2408, and pPFC0811 (P19). pPFC0055, trastuzumab heavy and light chain expression vector. 60S ribosomal protein gene L23 used as loading control (Liu et al., 2012). 30 cycles of PCR performed for NbAGO4a, 28 cycles for NbAGO4b. Nl ctrl, non-infiltrated control.
Figure 10:
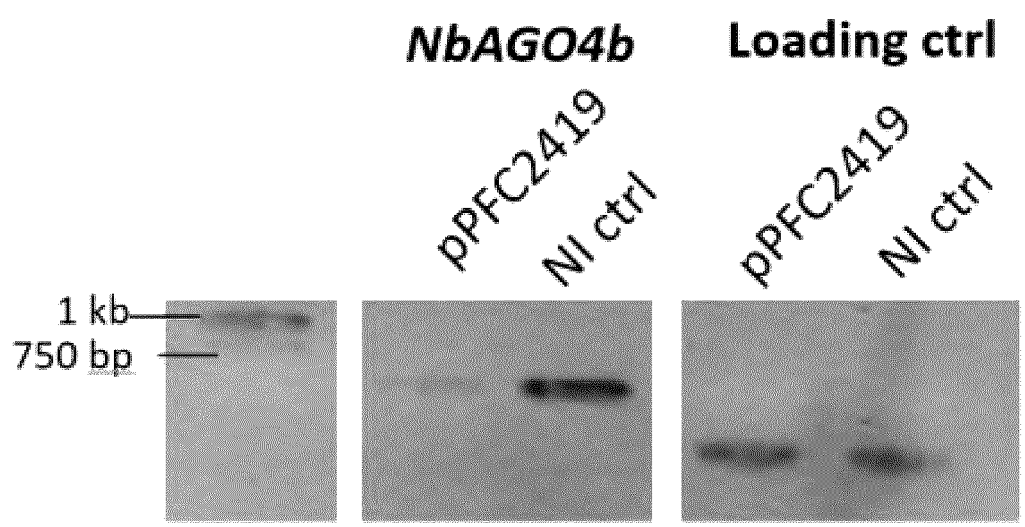
FIG. 10 shows semi-quantitative reverse transcription-PCR detection of NbAGO4b transcripts using cDNA from leaves spot infiltrated with pPFC2419. 60S ribosomal protein gene L23 used as loading control (Liu et al., 2012). 28 cycles of PCR performed. Nl ctrl, non-infiltrated control.

The *N. benthamiana* genome encodes two AGO1 genes, termed as AGO1-1 and AGO1-2 (also referred to as AGO1a and AGO1b). Two AGO4 genes also exist and are similarly named. Hairpins targeting NbAGO1b (pPFC2407; FIG. 1) and NbAGO4b (pPFC2408; FIG. 2) were constructed and suppression of NbAGO1a/b and NbAGO4a/b expression was determined by semi-quantitative reverse transcription-PCR (semi-qRT-PCR; FIG. 8-9). pPFC2407 efficiently suppressed both NbAGO1a and NbAGO1b, whereas pPFC2408 only partially suppressed NbAGO4a and NbAGO4b. pPFC2407 treatment appears to additionally suppress both NbAGO4 genes with comparable efficiency to pPFC2408. Off-target silencing by pPFC2407 was not anticipated as NbAGO1b and 4b share only 46% nucleotide identity, and the longest region of conserved similarity was only 11-nt. Alternatively, indirect effects on gene expression through feedback mechanisms cannot be excluded. To further improve NbAGO4 silencing, an additional NbAGO4-RNAi vector was constructed (pPFC2419; FIG. 3) and suppression of NbAGO4 expression was evaluated by semi-qRT-PCR (FIG. 10).

Recombinant Protein Yield

Figure 11:
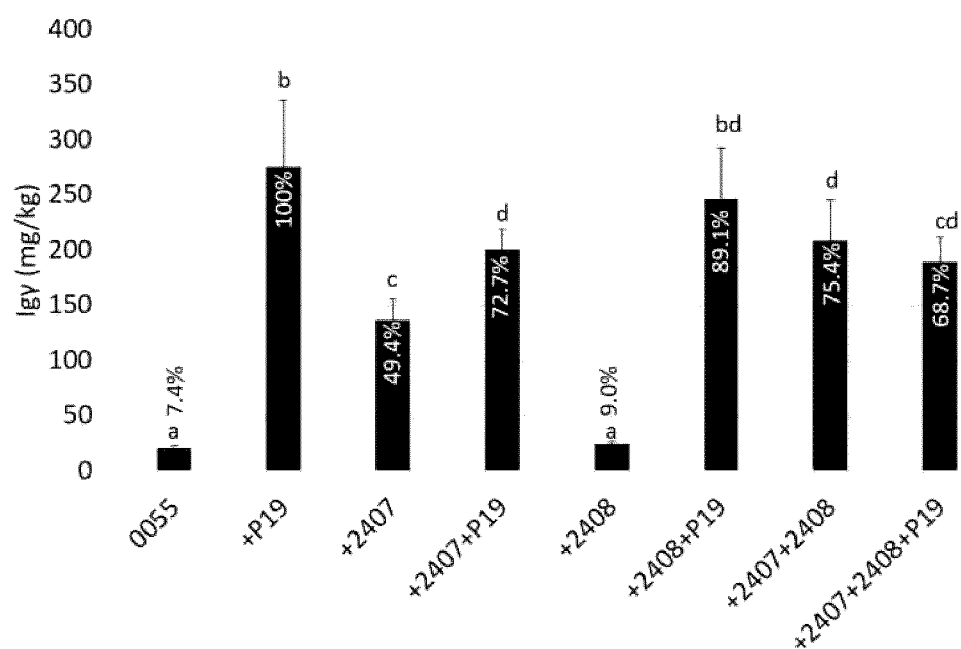
FIG. 11 shows improved trastuzumab expression by suppression of RNAi-induced post-transcriptional gene silencing. Trastuzumab light and heavy chains expressed by pPFC0055 alone or in combination with pPFC2407 (AGO1-RNAi), pPFC2408 (AGO4-RNAi) and/or (pPFC0811) (P19). Percent values in or above bars represent trastuzumab concentration relative to +P19 treatment. 7 days post-infiltration. Mean±SD. n=6 plants per treatment. One-way ANOVA, Tukey post-hoc.
Figure 12:
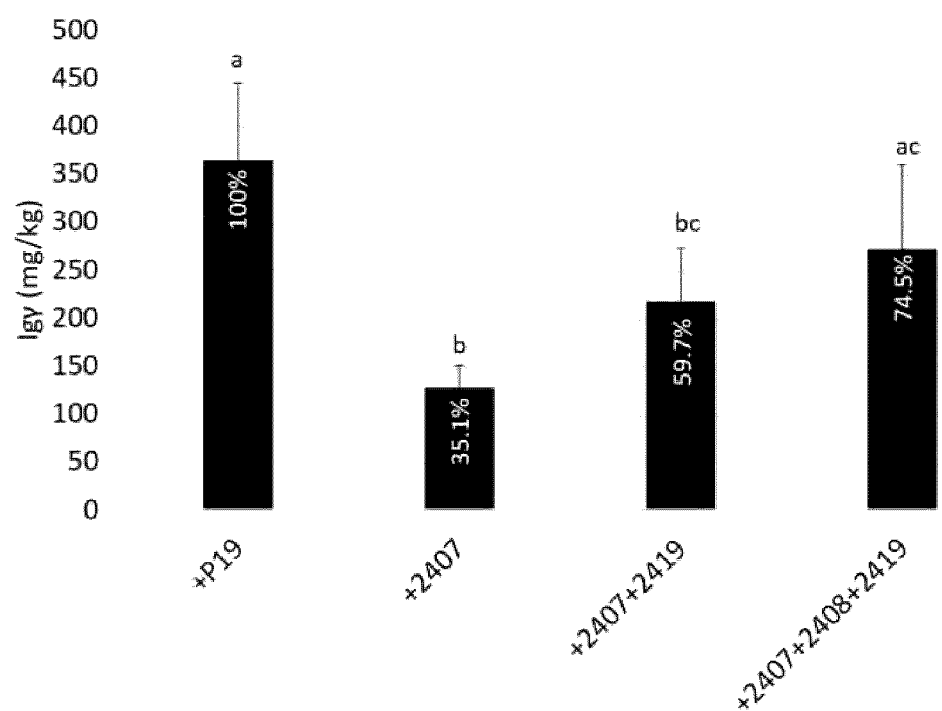
FIG. 12 shows improved trastuzumab expression by suppression of siRNA-induced post-transcriptional gene silencing. Trastuzumab light and heavy chains expressed by pPFC0055 in combination with pPFC2407 (AGO1-RNAi), pPFC2408 (AGO4-RNAi) and/or (pPFC1435) (P19). Percent values in or above bars represent trastuzumab concentration relative to +P19 treatment. 7 days post-infiltration. Mean±SD. n=5 plants per treatment. One-way ANOVA, Tukey post-hoc
Figure 13:
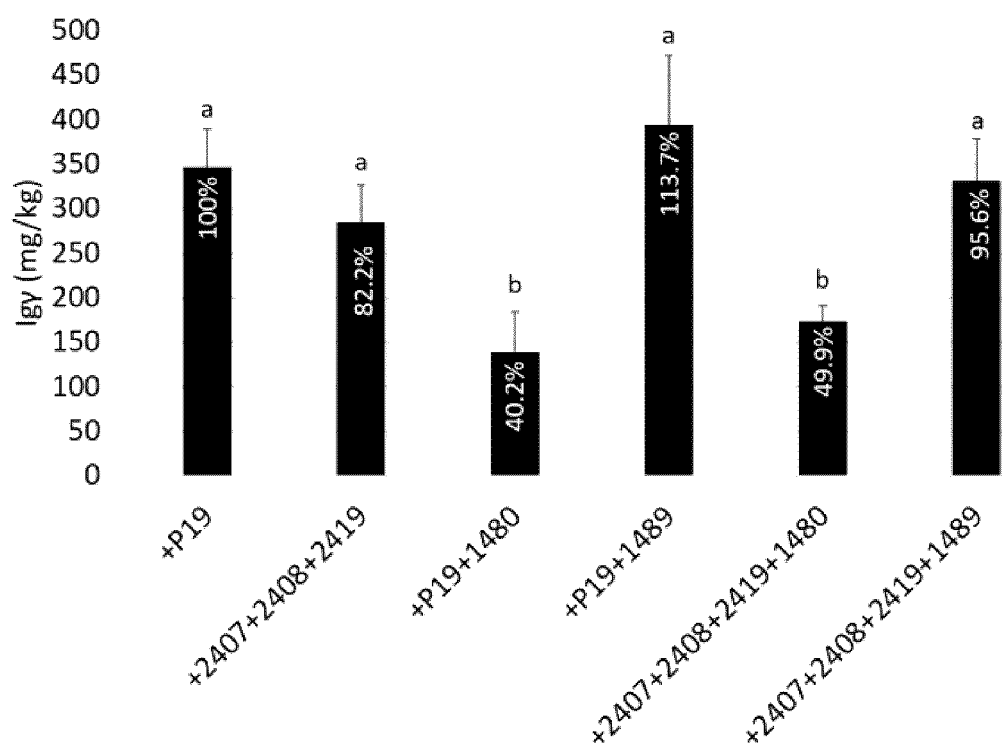
FIG. 13 shows the effect of co-expression of STT3D on trastuzumab concentration in combination with different methods for suppressing siRNA-induced post-transcriptional gene silencing. Trastuzumab light and heavy chains expressed by pPFC0055 in combinations with pPFC1435 (P19), pPFC2407 (AGO1-RNAi), pPFC2408 (AGO4-RNAi), pPFC2419 (AGO4-RNAi) and/or $P_{35S}$::STT3D (pPFC1480) or $P_{AtACT2}$::STT3D (pPFC1480). Percent values in or above bars represent trastuzumab concentration relative to +P19 treatment. 7 days post-infiltration. Mean±SD. n=4 plants per treatment. One-way ANOVA, Tukey post-hoc.

The RNAi plasmids pPFC2407, pPFC2408 and pPFC2419 were co-infiltrated with pPFC0055 (trastuzumab heavy and light chains, without P19) alone or in combinations with or without P19 (pPFC1435) (FIG. 11-13). AGO1-+AGO4-RNAi (2407+2408+2419) treatment produced consistent mg/kg yields, which were statistically equivalent to yields from P19 (pPFC1435 or pPFC0811 only) co-infiltration treatment (FIG. 12-13).

The effect of co-expression of STT3D on trastuzumab concentration in combination with different methods for suppressing siRNA-induced post-transcriptional gene silencing was also studied. The RNAi plasmids pPFC2407, pPFC2408 and pPFC2419 were co-infiltrated with pPFC0055 (trastuzumab heavy and light chains, without P19) alone or in combinations with or without $P_{35S}$::STT3D (pPFC1480) or $P_{AtACT2}$::STT3D (pPFC1489) (FIG. 13). 1489 ($P_{AtACT2}$-STT3D) slightly improves expression and reduces the percentage of aglycosylated HC (FIG. 14) compared to co-infiltration of 1480 (P35S::STT3D).

SUMMARY

Co-infiltration of pPFC0055 with pPFC2407 consistently improved recombinant protein yield over the unsuppressed silencing control (pPFC0055 without P19). This is unexpected as Odokonyero et al. (2017) reported RNAi suppression of NbAGO1 failed to increase the accumulation of the recombinant reporter protein GFP expressed by virus-derived expression vectors. In contrast, co-infiltration of pPFC0055 with pPFC2408 did not improve trastuzumab expression, consistent with the lack of GFP expression virus-derived expression vectors when NbAGO4 was silenced (Odokonyero et al., 2017).

The effect of pPFC2407 with pPFC2408 is surprising given the lack of effect of pPFC2408 alone on trastuzumab expression and is further unanticipated based on the lack of additive effects observed by Odokonyero et al. (2017) when different combinations of NbAGO genes were silenced. Trastuzumab yields are statistically equivalent to the P19 treatment when pPFC2407, pPFC2408 and pPFC2419 are applied together but not when only pPFC2407 and pPFC2408 are co-infiltrated (FIG. 11 compared to FIG. 12-13). Without being bound by theory, this finding suggests a hierarchy exists in regulating RNAi-mediate transgene silencing. When siRNA generation is uninhibited (i.e. AGO1 expression and function), the suppression of RNA-dependent DNA methylation (i.e. by AGO4 expression and function) is dispensable. However, when siRNA generation is interrupted (i.e. expression of a hairpin targeting AGO1 transcript), then RNA-dependent DNA methylation (i.e. by AGO4 expression and function) plays a significant role in repressing transgene expression. Thus, high transgene expression can only be achieved when both siRNA generation and RNA-dependent DNA methylation pathways are interrupted.

Example 2

Reducing Aglycosylation of Proteins Expressed in *Nicotiana benthamiana*

Minimizing aglycosylation of plant-produced recombinant proteins is desired since glycosylation of many recombinant proteins is required for either biological activity, protein conformational stability, or for enhanced circulatory retention. *Leishmania* STT3D has been shown to reduce aglycosylation of heterologous expressed antibodies in yeast systems (Choi et al., 2012).

FIG. 13 shows the effect of co-expression of LmSTT3D on trastuzumab concentration in combination with different methods for suppressing siRNAi-induced post-transcriptional gene silencing. LmSTT3D was expressed behind either the CaMV 35S strong promoter ($P_{35S}$::LmSTT3D; pPFC1480) or the less potent AtACT2 promoter ($P_{AtACT2}$::LmSTT3D; pPFC1489).

Expression of trastuzumab with the CaMV 35S promoter version of LmSTT3D showed a significant inhibition of expression yield (FIG. 13), independent of the system used to inhibit siRNAi-induced post-translational gene silencing (i.e., P19 or AGO1 and AGO4 RNAi). Use of the less potent AtACT2 promoter does not show this effect and restores expression, independent of the system used to inhibit post-translational gene silencing.

Figure 14:
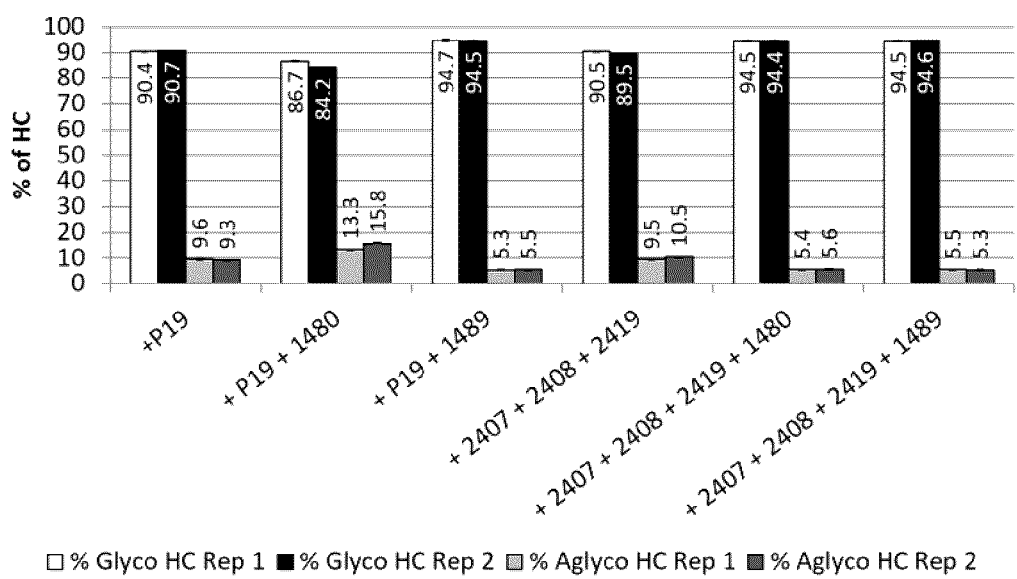
FIG. 14 shows the effect of co-expression of STT3D in combination with different methods for suppressing siRNA-induced post-transcriptional gene silencing on percent glycosylation of trastuzumab heavy chain. Trastuzumab light and heavy chains expressed by pPFC0055 in combinations with pPFC1435 (P19), pPFC2407 (AGO1-RNAi), pPFC2408 (AGO4-RNAi), pPFC2419 (AGO4-RNAi) and/or $P_{35S}$::STT3D (pPFC1480) or $P_{AtACT2}$::STT3D (pPFC1480). Percent glycosylation or aglycosylation indicated in or above the bars. 7 days post-infiltration.

FIG. 14 shows the effect of co-expression of STT3D in combination with different methods of post-transcriptional gene silencing on percent aglycosylation of trastuzumab heavy chain.

It was found that pPFC1489 ($P_{AtACT2}$::LmSTT3D) reduced aglycosylated heavy chain by 50% compared to no LmSTT3D or pPFC1480 ($P_{35S}$::LmSTT3D). However, when AGO1 and AGO4 were silenced (pPFC2407+pPFC2408+pPFC2419), pPFC1480 ($P_{35S}$::LmSTT3D) produced an equivalent improvement in aglycosylation to pPFC1489. Without being bound by theory, this may be because P19 (pPFC1435) enables higher expression of LmSTT3D when driven by the CaMV 35S promoter.

Methods for Examples 1 and 2

RNA Extraction and cDNA Preparation

Total RNA was extracted from *N. benthamiana* leaves using a RNeasy Plant Mini Kit (Qiagen). RNA concentration was estimated using a NanoDrop 2000c (ThermoScientific). First strand cDNA synthesis was performed using SuperScript II (Invitrogen).

Vector Construction

The *N. benthamiana* genome encodes two NbAGO1 genes, termed as NbAGO1-1 and NbAGO1-2 (also referred to as NbAGO1a and NbAGO1b). Two NbAGO4 genes also exist and are similarly named. Hairpins targeting NbAGO1 (pPFC2407; FIG. 1) and NbAGO4 (pPFC2408 and pPFC2419; FIGS. 2 and 3) were constructed using cDNA fragments (SEQ ID NO:5-7) from the respective target genes placed in sense and antisense orientation on either side of the second intron from Arabidopsis thaliana beta-1,2-xylosyltransferase (SEQ ID NO:8). The hairpins were cloned into PlantForm's proprietary pFBin vector backbone. The vectors were transformed into Agrobacterium tumefaciens EHA105 (also referred to as Agrobacterium tumefaciens AT564) by electroporation.

The Leishmania major STT3D (LmSTT3D; GenBank XP_003722509) sequence was codon optimized for expression in N. benthamaina by GeneArt (Invitrogen) and the open-reading frame synthesized (GeneWiz; SEQ ID NO:3). The ORF was cloned into PlantForm's proprietary pFBin vector backbone (pPFC1480; FIG. 4). pPFC1480 was further modified; the CaMV 35S promoter was replaced with the AtACT2 promoter and 5'-UTR from Arabidopsis thaliana (SEQ ID NO:9; pPFC1489; FIG. 5).

Plant Cultivation

PlantForm's proprietary transgenic Nicotiana benthaniama var 'KDFX' were grown from seed in Sunshine Mix LA4 potting soil in a greenhouse at the University of Guelph (Guelph, Canada). The greenhouses were maintained at 20-25° C. with supplemental light from high-pressure sodium lamps to ensure a 16-hr photoperiod. The plants were watered as needed with Plant-Prod 20-8-20 High Nitrate Fertilizer solution (250 ppm Nitrogen, EC 2.5 mS/cm, pH 6.0). When seedlings reached at least 2.5 cm in height, they were transplanted into 3.5" square pots. Approximately 4-weeks after seeding, the plants were infiltrated with recombinant A. tumefaciens.

Whole Plant and Spot Infiltrations

A. tumefaciens containing pPFC2407 (AGO1-RNAi), pPFC2408 (AGO4-RNAi), pPFC2419 (AGO4-RNAi), pPFC0055 (trastuzumab heavy and light chain genes), pPFC0811 (P19) or pPFC1435 (P19) were grown in LB media containing 50 µg/mL kanamycin and 50 µg/mL rifampicin at 28° C. in a rotary shaker at 200 rpm for approximately 17-hours. A. tumefaciens cultures were diluted with infiltration buffer (10 mM MES, 100 mM MgSO$_4$, pH 5.5) to achieve of final OD$_{600}$ of 0.2 for each strain in a 2 L infiltration cocktail. Combinations of A. tumefaciens were prepared to achieve the desired treatments, thus treatments had a total OD$_{600}$>0.2. The treatments are indicated by vector numbers in FIGS. 8-14. The infiltration cocktails were placed in a custom build vacuum chamber and decompressed for 5 minutes at 28-28.5 mmHg. Four-week-old N. benthamiana plants were inverted into the buckets containing 2 L of infiltration cocktail and a vacuum of 28-28.5 mmHg was applied for 2 min, after which the plants were removed and placed in a controlled environment growth chamber [conditions comparable to greenhouse in which plants were grown; see above]. Spot infiltrations were similarly performed using a 3 cc syringe, instead of a vacuum chamber, to introduce recombinant A. tumefaciens into plant leaves. However, spot infiltrated A. tumefaciens was pelleted out of the culture medium by centrifugation at 10000×g for 10 min at 4° C. and resuspended in infiltration buffer at an OD$_{600}$ of 0.2.

Suppression of NbAGO1 and NbAGO4

Total RNA was extracted from spot infiltrated leaves and first strand cDNA prepared as described above. Suppression of NbAGO1a/b and NbAGO4a/b expression was estimated by semi-quantitative reverse transcription-PCR (semi-qRT-PCR; FIG. 8-10). Amplification was performed using 5× Taq Master Mix (New England Biolabs, Cat. M0285) and 0.2 µM each of forward and reverse primers (Table 2). PCR program: 1) 95° C. 30 sec, 2) 95° C. 30 sec, 59° C. 30 sec, 68° C. 1 min; run for 28 or 30 cycles. DNA was stained with EZ-Vision® Two (Amresco, Cat. N650). 1% agarose gels were visualized on a Gel-Doc Universal Hood II (Bio-Rad) using the Highlight Saturated Pixels function to improve accuracy (Quantity One software v 4.6.7, Bio-Rad). Amplicons were purified and sequenced to confirm primer specificity.

Recombinant Protein Yield and Total Soluble Protein Quantification

Infiltrated plants were harvested at 7 days post-infiltration. Leaves were removed from each plant, separately bagged and stored at −80° C. Total frozen leaf tissue from each plant was homogenized for 30-60 sec in 1×PBS (3:1 v/w ratio) using a polytron homogenizer (Brinkmann Instruments, Polytron Model PT10/35). Aliquots were centrifuged at 20000× g for 20 min at 4° C. Total soluble protein concentration was determined by Bradford Assay (Bradford, 1976). Recombinant trastuzumab concentration was determined using a BLItz system (Pall ForteBio) with protein A biosensor tips and a 0.5-150 µg/mL standard curve prepared with human Igγ (Pall ForteBio).

Weak Cation Exchange High Performance Liquid Chromatography (WCX-HPLC)

Soluble protein supernatant was applied to protein G spin traps (GE Life Sciences, Cat. 28-4083-47). Eluates were dialyzed overnight in 1× PBS, pH 7.4 at 4° C. The samples were diluted to 1 mg/mL with 1×PBS, pH 7.4 and 10 µg of protein was injected at a flow rate of 1 mL/min into a BioMab NP5 WCX column (P/N 5190-2405; Agilent). Mobile phase A consisted of 10 mM sodium acetate, pH 4.4 and mobile phase B was 10 mM sodium acetate, pH 4.4 with 1 M sodium chloride (NaCl). A gradient increase of 1% NaCl per minute over 40 minutes was used to separate the fully glycosylated (eluted first), hemi-glycosylated, and aglycosylated product (eluted last; Table 3). Detection was acquired at 280 nm. Each sample was injected twice, and overlaid to ensure run consistency prior to the peak integration measurements. The Agilent OpenLab, ChemStation edition, integration tool was used to estimate the relative percentage of each form. The baseline and retention time cut-offs for each peak were held consistent for each chromatogram to achieve a comparable dataset, after ensuring similar retention times between runs and samples.

TABLE 1

Sequences used in vector construction

| SEQ ID # | Description | Sequence (5'->3') |
|---|---|---|
| 1 | *Arabidopsis thaliana* basic chitinase signal peptide (Genbank accession: NP_566426) | MAKTNLFLFLIFSLLLSLSSA |
| 2 | *Homo sapien* butyryl-cholinesterase signal peptide (GenBank accession: AAA99296.1) | MHSKVTIICIRFLFWFLLLCMLIGKSHT |
| 3 | *Leishmania major* STT3D open reading frame used in vectors pPFC1480 and pPFC1489 | ATGGGTAAGCGTAAGGGCAACAGCCTTGGTGATTCTGGTTCTGCTG CTACCGCTTCTAGAGAGGCTTCTGCTCAAGCTGAAGATGCTGCTTC TCAGACCAAGACTGCTAGCCCTCCTGCTAAGGTTATCCTGCTTCCT AAGACCTTGACCGACGAGAAGGACTTTATCGGGATCTTCCCTTTTC CGTTCTGGCCTGTGCATTTCGTGCTTACTGTTGTGGCTCTTTTCGTG CTGGCTGCTTCTTGCTTTCAGGCTTTCACCGTGAGGATGATCAGCG TGCAGATCTACGGTTACCTGATCCACGAGTTCGACCCGTGGTTTAA TTACAGGGCTGCCGAGTACATGTCTACCCATGGTTGGTCTGCTTTC TTCAGCTGGTTCGACTACATGAGCTGGTATCCTCTTGGTAGGCCTG TGGGTTCTACTACTTATCCTGGACTTCAGCTTACCGCTGTGGCTATT CATAGAGCTTTGGCTGCTGCTGGCATGCCGATGTCTCTTAACAATG TGTGCGTGCTGATGCCTGCATGGTTCGGTGCTATTGCTACTGCTAC TTTTGGCCTTCTGTACCTACGAGGCTTCAGGTTCTACTGTTGCTGCT GCAGCTGCTGCTCTGAGCTTCTCTATTATTCCTGCTCACCTGATGC GGAGCATGGCTGGTGAATTTGACAACGAGTGCATTGCTGTGGCTG CTATGCTTCTGACTTTCTACTGCTGGGTGAGATCCCTTAGGACCAG ATCTTCTTGGCCTATTGGTGTGCTTACCGGTGTTGCTTACGGTTACA TGGCTGCAGCTTGGGGCGGTTACATTTTCGTGTTGAACATGGTGGC TATGCACGCCGGCATTAGCTCTATGGTTGATTGGGCTCGTAATACT TACAACCCGAGCCTTCTTAGGGCTTACACCCTTTTCTACGTGGTGG GAACCGCTATTGCTGTTTGTGTTCCTCCTGTGGGCATGAGCCCTTT CAAGTCTCTTGAACAGCTTGGTGCTCTGCTGGTGCTTGTTTTCTTGT GCGGACTTCAGGTTTGCGAGGTGTTGAGAGCTAGAGCTGGTGTTG AGGTTAGGTCCAGGGCTAACTTCAAGATCAGAGTGAGGGTGTTCTC CGTTATGGCTGGCGTTGCAGCTCTTGCTATTTCTGTGCTTGCTCCT ACCGGTTACTTCGGTCCTTTGTCTGTTAGGGTGAGAGCCTTGTTCG TTGAGCATACCAGGACTGGTAACCCTCTGGTTGATTCTGTTGCTGA GCATCAGCCTGCTTCTCCAGAGGCTATGTGGGCTTTTCTTCATGTG TGCGGTGTGACTTGGGGTCTGGGTTCTATTGTGTTGGCTGTGTCTA CCTTCGTGCACTACAGCCCTTCTAAGGTGTTCTGGCTTCTGAACTC TGGCGCCGTGTACTACTTCTCTACTAGGATGGCTAGGCTCCTGCTT CTTTCTGGACCTGCTGCTTGTCTTAGCACCGGTATTTTCGTGGGCA CCATTCTTGAAGCTGCCGTGCAGTTGTCTTTCTGGGATTCTGATGC TACCAAGGCCAAAAAGCAGCAAAAGCAGGCTCAGAGGCATCAGAG AGGTGCTGGTAAAGGTTCTGGTAGGGATGACGCTAAGAATGCTACT ACCGCTCGGGCTTTCTGTGATGTGTTTGCTGGTTCTTCTCTGGCTT GGGGTCACCGTATGGTGCTTTCTATTGCAATGTGGGCTCTTGTGAC TACCACCGCCGTTTCTTTCTTCTCCTCCGAATTCGCTTCCCACAGCA CTAAGTTCGCTGAGCAGTCAAGCAACCCGATGATTGTGTTCGCTGC TGTTGTGCAGAATCGTGCTACTGGCAAGCCTATGAACCTGCTGGTG GATGATTACCTGAAGGCTTACGAGTGGCTGAGGGATTCTACTCCTG AGGATGCTAGAGTTCTCGCTTGGTGGGATTACGGCTACCAGATTAC CGGTATTGCAACAGGACCTCTCTGGCTGATGGTAATACTTGGAAC CACGAGCACATTGCCACCATCGGTAAGATGCTTACTAGCCCTGTTG TCGAGGCTCACTCTCTTGTTAGGCACATGGCTGATTACGTGCTGAT TTGGGCTGGTCAGTCTGGCGATCTTATGAAGTCTCCTCACATGGCT AGGATCGGCAACTCTGTGTACCACGATATCTGCCCTGATGATCCTC TTTGCCAGCAGTTCGGTTTCCACCGGAATGATTACTCTCGGCCTAC TCCTATGATGCGGGCTTCTCTTCTTTACAACCTTCACGAGGCTGGT AAGCGGAAAGGTGTTAAGGTGAACCCGAGCTTGTTCCAAGAGGTG TACAGCTCTAAGTACGGCCTGGTGAGGATCTTCAAGGTGATGAATG TGAGCGCCGAGAGCAAGAAGTGGGTTGCAGATCCTGCTAATAGGG TGTGCCATCCTCCTGGTTCTTGATTTGTCCTGGTCAGTACCCTCC GGCCAAAGAAATTCAAGAGATGCTGGCTCATAGGGTGCCGTTCGAT CAGGTTACCAACGCTGATCGGAAGAACAACGTGGGGTCTTATCAAG AGGAGTACATGCGGAGGATGCGTGAGTCTGAGAATAGAAGG |

TABLE 1-continued

Sequences used in vector construction

| SEQ ID # | Description | Sequence (5'->3') |
|---|---|---|
| 4 | Tomato Bushy Stunt Virus (TBSV) P19 nucleotide sequence codon-optimized for expression in Nicotiana. (Non-codon optimized sequence Genbank accession: M21958) | ATGGAAAGGGCTATTCAGGGAAATGATGCTAGAGAGCAGGCTAATT CTGAAAGATGGGATGGTGGATCTGGTGGAACTACTTCTCCATTCAA GCTTCCAGATGAGTCTCCATCTTGGACTGAGTGGAGGCTTCATAAC GATGAGACTAACTCCAATCAGGATAACCCACTCGGATTCAAAGAAT CTTGGGGATTCGGAAAGGTTGTGTTCAAGCGTTACCTTAGGTATGA TAGGACTGAGGCTTCACTTCATAGGGTTCTCGGATCTTGGACTGGT GATTCTGTTAACTACGCTGCTTCTCGTTTTTTTGGATTCGATCAGAT CGGATGCACTTACTCTATTAGGTTCAGGGGAGTGTCTATTACTGTTT CTGGTGGATCTAGGACTCTTCAACACCTTTGCGAGATGGCTATTAG GTCTAAGCAAGAGCTTCTTCAGCTTGCTCCAATTGAGGTTGAGTCT AACGTTTCAAGAGGATGTCCAGAAGGTACTGAGACTTTCGAGAAAG AATCCGAGTGA |
| 5 | Nicotiana benthamiana AGO1b fragment used in vector pPFC2407 | GAGTCGTCTCACAGTGCTGTTTGACAAAACATGTATTTAAGATGAGC AAACAGTATCTAGCCAATGTAGCGCTGAAAATCAATGTGAAGGTGG GAGGGAGAAACACTGTGCTTGTTGATGCAATATCGAGGCGAATTCC TCTTGTCAGCGACCGGCCTACCATCATTTTTGGTGCAGATGTCACC CACCCTCACCCTGGGGAGGACTCTAGCCCATCCATTGCCGCGGTG GTTGCTTCTCAAGATTGGCCTGAGATTACAAAGTATGCTGGTCTAGT TTCTGCTCAAGCCCATAGGCAAGAGCTTATTCAGGATCTGTACACG ACTAGGCAAGATCCTGTTAAGGGGACAGTTGCTGGTGGAATGATTA AGGACTTACTTATATCCTTCCGAAGAGCTACTGGACAAAAGCCCCA GAGAATAATTTTCTATAGGGATGGTGTTAGTGAAGGACAATTTTATC AAGTGCTTCTGTTCGAACTTGATGCGATCCGCAAAGCATGTGCGTC TTTGGAGCCAAATTATCAGCCCCCAGTCACATTTGTTGTGGTTCAGA AACGACATCACACAAGGCTTTTTGCCAATAACCACCGTGACAGAAA TGCAGTTGACAGGAGCGGGAACATTATACCTGGTACTGTTGTAGAT TCAAAGATATGCCACCCGACAGAGTTTGATTTCTATCTTTGTAGCCA TGCCGGCATACAGGGTACGAGCCGTCCAGCTCACTACCATGTTCTA TGGGACGAGAACAAATTCACAGCCGATGCGCTGCAGTCTTTGACCA ACAACCTCTGCTATACATATGCAAGGTGCACGCGTTCCGTCTCCAT CGTTCCCCCTGCATATT |
| 6 | Nicotiana benthamiana AGO4b fragment used in vector pPFC2408 | CAGGAGAGGATGCAAGTCCTAAGCAATGCCCTCAAAATCAACAAAT ATGATGCCGAGCCTCTGCTTCGTGCCTGTGGAATTTCAATCAGCAG TAACTTCACCCAGGTTGAAGGGCGTGTTCTTTCTCCCCCAAAGTTG AAGACAGGTGGTGATGACTTTGTTCCCCGTAATGGCAGGTGGAATT TCAATAACAAGAGACTGGTCGATCCTACCAAGATAGAGCGTTGGGC TGTTGTCAACTTTTCTGCACGTTGTAACATACAAGGGCTAATCAGTG ATCTTATAAAATGTGGGAAAATGAAAGGAATTATGGTGGAAGATCCA TTTGATGTTTTTGAAGAGTCTCCACAATTCAGAAGGGCTCCGCCACT TGTCAGAGT |
| 7 | Nicotiana benthamiana AGO4b fragment used in vector pPFC2419 | GAGCTTCAGTGCGCACCCAGTCTCCTAAAGTGGAGATGATAGACAA CTTGTTTAAACGTGCTTCTGACACTGAGGATGAGGGGATAATGAGG GAGGCTTTGCTAGATTTTTATGTGAGTTCTGGAAAAAGGAAGCCTG AGCATATATTATATATTCAGGGATGGTGTCAGTGAATCTCAATTTAAT CAAGTTCTGAACATTGAACTGGATCAGATCATTGAGGCGTGTAAATT TCTCGACGAGAAGTGGTCACCAAAGTTT |
| 8 | Arabidopsis thaliana beta-1,2-xylosyl-transferase intron (Genbank accession: CP002688; TAIR accession: AT5G55500) | CACTGCACGGTATGCTCCTCTTCTTGTTCATGGTCATGATCCTTATA TGAGCAGGGAAAGTCCAGTTTAGACTTGTAGTTAGTTACTCTTCGTT ATAGGATTTGGATTTCTTGCGTGTTTATGGTTTTAGTTTCCCTCCTTT GATGAATAAAATTGAATCTTGTATGAGTTTCATATCCATGTTGTGAAT CTTTTTGCAGACGCAGCTAG |
| 9 | Arabidopsis thaliana ACT2 promoter and 5'-UTR used in vector pPFC1489 (Genbank accession: U41998) | TGATTCAGAATCGTTTTGACGAGTTCGGATGTAGTAGTAGCCATTAT TTAATGTACATACTAATCGTGAATAGTGAATATGATGAAACATTGTAT CTTATTGTATAAATATCCATAAACACATCATGAAAGACACTTTCTTTC ACGGTCTGAATTAATTATGATACAATTCTAATAGAAAACGAATTAAAT TACGTTGAATTGTATGAAATCTAATTGAACAAGCCAACCACGACGAC GACTAACGTTGCCTGGATTGACTCGGTTTAAGTTAACCACTAAAAAA ACGGAGCTGTCATGTAACACGCGGATCGAGCAGGTCACAGTCATG AAGCCATCAAAGCAAAAGACTAATCCAAGGGCTGAGATGATTAAT TAGTTTAAAAATTAGTTAACACGAGGGAAAAGGCTGTCTGACAGCC AGGTCACGTTATCTTTACCTGTGGTCGAAATGATTCGTGTCTGTCGA TTTTAATTATTTTTTGAAAGGCCGAAAATAAAGTTGTAAGAGATAAA CCCGCCTATATAAATTCATATATTTTCCTCTCCGCTTTGAATTGTCTC GTTGTCCTCCTCACTTTTCATCAGCCGTTTTGAATCTCCGGCGACTTG |

TABLE 1-continued

Sequences used in vector construction

| SEQ ID # | Description | Sequence (5'->3') |
|---|---|---|
| | | ACAGAGAAGAACAAGGAAGAAGACTAAGAGAGAAAGTAAGAGATAA TCCAGGAGATTCATTCTCCGTTTTGAATCTTCCTCAATCTCATCTTCT TCCGCTCTTTCTTTCCAAGGTAATAGGAACTTTCTGGATCTACTTTA TTTGCTGGATCTCGATCTTGTTTTCTCAATTTCCTTGAGATCTGGAA TTCGTTTAATTTGGATCTGTGAACCTCCACTAAATCTTTTGGTTTTAC TAGAATCGATCTAAGTTGACCGATCAGTTAGCTCGATTATAGCTACC AGAATTTGGCTTGACCTTGATGGAGAGATCCATGTTCATGTTACCTG GGAAATGATTTGTATATGTGAATTGAAATCTGAACTGTTGAAGTTAG ATTGAATCTGAACACTGTCAATGTTAGATTGAATCTGAACACTGTTT AAGGTTAGATGAAGTTTGTGTATAGATTCTTCGAAACTTTAGGATTT GTAGTGTCGTACGTTGAACAGAAAGCTATTTCTGATTCAATCAGGGT TTATTTGACTGTATTGAACTCTTTTGTGTGTTTGCAG |

TABLE 2

Primer sequences

| Primer number | Primer Name | SEQ ID # | Sequence (5'->3') |
|---|---|---|---|
| 1 | EMnbAGO1a-618-F | 10 | CGAACCAACGACACAGCAAG |
| 2 | EMnbAGO1a-1356-R | 11 | GCTGGCTCACGAAGTCAATA |
| 3 | EMnbAGO1b-523-F | 12 | GCTGCAATGACTACTCAGCC |
| 4 | EMnbAGO1b-1367-R | 13 | GTCTAGATGGCACATCTCGGT |
| 5 | EMnbAGO4a-502-F | 14 | CCTGGCAAACATGGAAGTCC |
| 6 | EMnbAGO4a-1375-R | 15 | TTGCTACTGATTGAGACGCC |
| 7 | EMnbAGO4b-813-F | 16 | GCTTTAGGACCACTCAGAGTG |
| 8 | EMnbAGO4b-1306-R | 17 | GGGCATTGCTTAGGACTTGC |

TABLE 3

WCX-HPLC gradient conditions

| Step | Time | % A | % B |
|---|---|---|---|
| Elution | 0 min | 90% | 10% |
| | 40 min | 50% | 50% |
| Column Strip | 45 min | 0% | 100% |
| | 50 min | 0% | 100% |
| Equilibration | 55 min | 90% | 10% |
| | 65 min | 90% | 10% |

Example 3

Improved Yields from AGO-RNAi Silencing Suppression

In Examples 1 and 2, the AGO1 and AGO4-RNAi vectors were transformed into two different *Agrobacterium* strains; pPFC2407 and pPFC2408 were in *Agrobacterium* AT542 and pPFC2419 was in the 'old' accession of *Agrobacterium* AT564, which lacked a verified chain of custody from the laboratory of origin (i.e pPFC #). Here, all three vectors were transformed into the 'new' *Agrobacterium* AT564 accession, which has a verified chain of custody from the laboratory of origin (i.e. pPFC #A). Following this change, AGO-RNAi produced equivalent or better yields compared to the P19 control in three consecutive experiments (Table 4).

TABLE 4

| Exp | Treatment (pPFC0055A+) | Stripped Leaves FW (g) | Tmab (mg/kg) | Tmab (mg/plant) | TSP (µg/mL) | TSP (mg/plant) |
|---|---|---|---|---|---|---|
| 17-09-14 | +1435A | 19.5 ± 3 | 229.1 ± 31.5 | 4.0 ± 1.0 | 1172.4 ± 57.4 | 86.31 ± 14.9 |
| | +2407 + 2408 + 2419 | 20.5 ± 1.1 | 174.6 ± 25.9 | 3.2 ± 0.5 | 1251.9 ± 90.1 | 95.02 ± 10.0 |
| 18-01-19 | +1435A | 11.9 ± 2.3 | 345.7 ± 56.4 | 4.0 ± 0.5 | 1812.2 ± 84.2 | 86.9 ± 17.3 |
| | +2407 + 2408 + 2419 | 13.6 ± 1.7 | 319.2 ± 71.3 | 4.3 ± 1.0 | 1660.9 ± 147.9 | 92.75 ± 14.9 |
| | +2407A + 2408A + 2419A | 13.7 ± 4.2 | 430.8 ± 61.8 | 5.7 ± 1.1 | 1881.9 ± 134.9 | 105.7 ± 29.8 |
| 18-02-14 | +1435A | 16.2 ± 1.8 | 235.2 ± 32.8 | 3.4 ± 0.2 | 1629.5 ± 151.1 | 96.76 ± 12.2 |
| | +2407A + 2408A + 2419A | 15.5 ± 2.9 | 283.5 ± 29.8 | 4.0 ± 0.6 | 1658.1 ± 104.4 | 97.3 ± 24.5 |
| 18-03-07 | +1435A | 19.0 ± 1.7 | 369.9 ± 33.9 | 7.0 ± 1.0 | 1735.1 ± 88.3 | 137.5 ± 13.0 |
| | +2407 + 2408 + 2419 | 18.9 ± 2.9 | 311.2 ± 43.6 | 6.0 ± 1.6 | 1662.7 ± 115.2 | 131.5 ± 28.5 |
| | +2407A + 2408A + 2419A | 18.2 ± 2.7 | 347.2 ± 44.0 | 6.3 ± 0.7 | 1732.6 ± 158.6 | 130.5 ± 14.4 |

Gene Expression Analysis

Expression of NbAGO1a, NbAGO1b, NbAGO4a, NbAGO4b, trastuzumab light chain and trastuzumab heavy chain genes following infiltration with AGO1- and/or AGO4-RNAi vectors using *Agrobacterium tumefaciens* strain AT564 was determined using quantitative real-time polymerase chain reaction.

Treatments were: 1) infiltration buffer only ("B"), 2) pPFC0055A only, 3) pPFC0055A+pPFC1435A (P19), 4) pPFC0055A+pPFC2407 (AGO1-RNAi), 5) pPFC0055A+pPFC2408 (AGO4-RNAi1), 6) pPFC0055A+pPFC2419 (AGO4-RNAi3), 7) pPFC0055A+pPFC2407+pPFC2408, and 8) pPFC0055A+pPFC2407+pPFC2408+pPFC2419.

Trastuzumab yield and total soluble protein concentrations were consistent with previous infiltrations.

Figure 15:
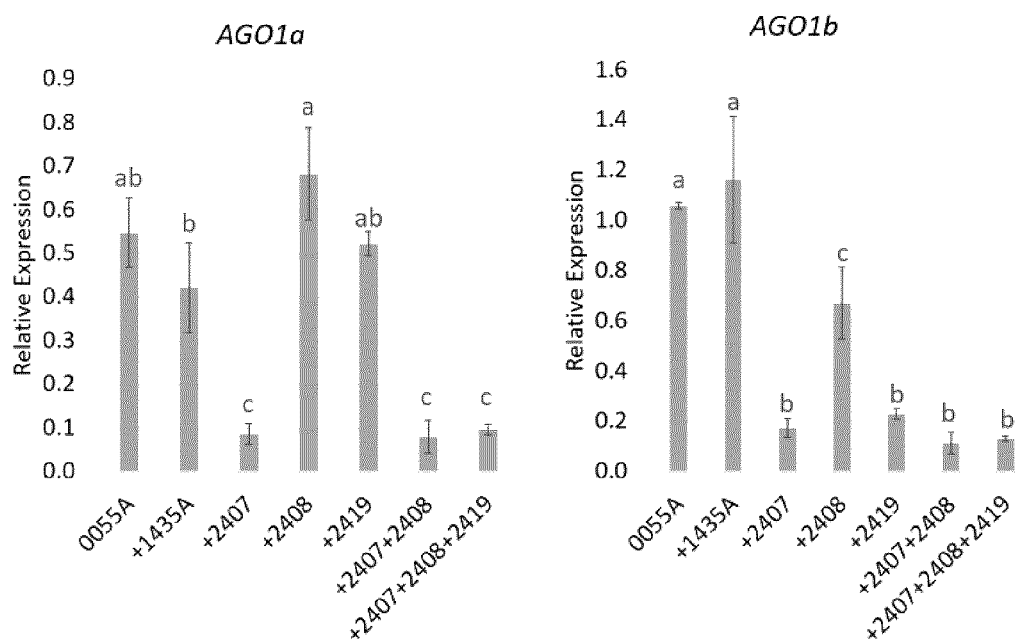
FIG. 15 shows expression of NbAGO1a and NbAGO1b in *Nicotiana benthamiana* KDFX in response to infiltration with *Agrobacterium* AT564 containing various T-DNA vectors. Treatments were: buffer only pPFC0055A only, pPFC0055A+pPFC1435A (P19), pPFC0055A+pPFC2407 (AGO1-RNAi1), pPFC0055A+pPFC2408 (AGO4-RNAi1), pPFC0055A+pPFC2419 (AGO4-RNAi3), pPFC0055A+pPFC2407+pPFC2408, and pPFC0055A+pPFC2407+pPFC2408+pPFC2419. Total RNA extracted from age-matched leaves from three biological replicates. Two technical replicates performed. Mean±SD. One-way ANOVA, Tukey-post hoc (p<0.0001). Relative expression determined by ΔΔCt method (Pfaffl 2001). "Buffer only" control set as R=1. L23 (ribosomal 60S) used as reference gene (Liu et al 2012). Note, pPFC0055 and pPFC0055A are the same vector. The "A" suffix denotes the accession of Agrobacterium harboring the vector, either an accession without or with a verified chain of custody from the laboratory of origin, respectively. The same applies for other vector designations.

Infiltration with pPFC2407 reduced transcription of AGO1a and AGO1b by about 85-90% (FIG. 15). Infiltration with pPFC2408 or pPFC2419 suppressed AGO1b by about 40% or 75% (FIG. 15), respectively. This suggests pPFC2419 is almost as effective as pPFC2407 at suppressing AGO1b. Without being bound by theory, this could indicate either an off-target affect or feedback mechanism. The pPFC2419 hairpin does contain an 18-nucleotide sequence with homology to AGO1b, meaning an off-target affect is theoretically possible. However, no such similarity exists between the pPFC2408 hairpin and AGO1b, suggesting a feedback mechanism could be involved.

Figure 16:
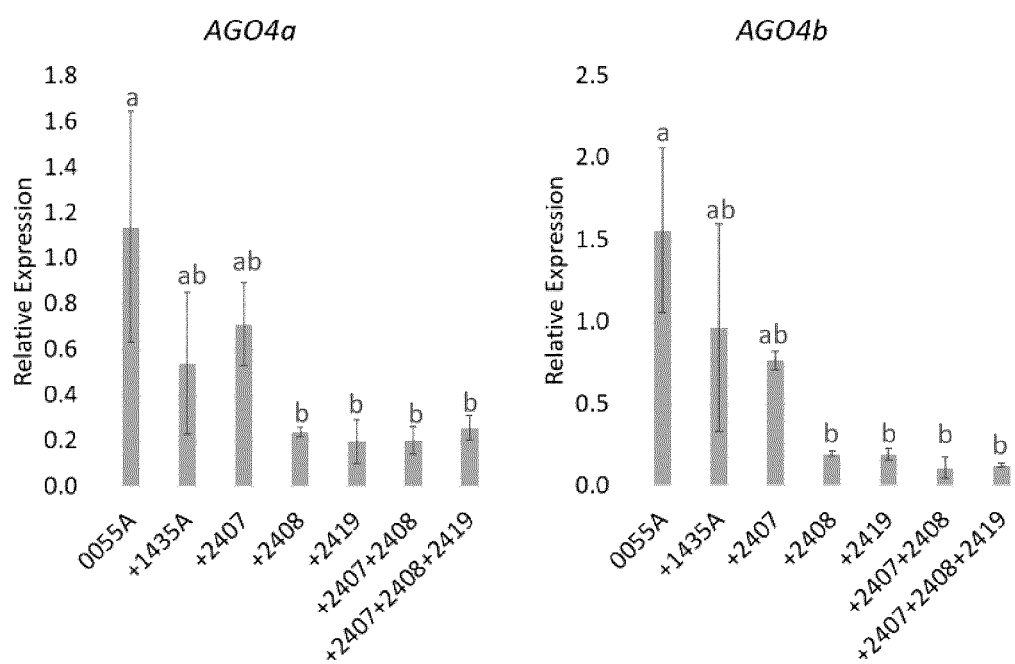
FIG. 16 shows expression of NbAGO4a and NbAGO4b in Nicotiana benthamiana KDFX in response to infiltration with Agrobacterium AT564 containing various T-DNA vectors. Treatments were: buffer only pPFC0055A only, pPFC0055A+pPFC1435A (P19), pPFC0055A+pPFC2407 (AGO1-RNAi1), pPFC0055A+pPFC2408 (AGO4-RNAi1), pPFC0055A+pPFC2419 (AGO4-RNAi3), pPFC0055A+pPFC2407+pPFC2408, and pPFC0055A+pPFC2407+pPFC2408+pPFC2419. Total RNA extracted from age-matched leaves from three biological replicates. Two technical replicates performed. Mean±SD. One-way ANOVA, Tukey-post hoc (AGO4a p=0.0019; AGO4b p=0.0003). "Buffer only" control set as R=1. L23 (ribosomal 60S) used as reference gene (Liu et al 2012).
Figure 17:
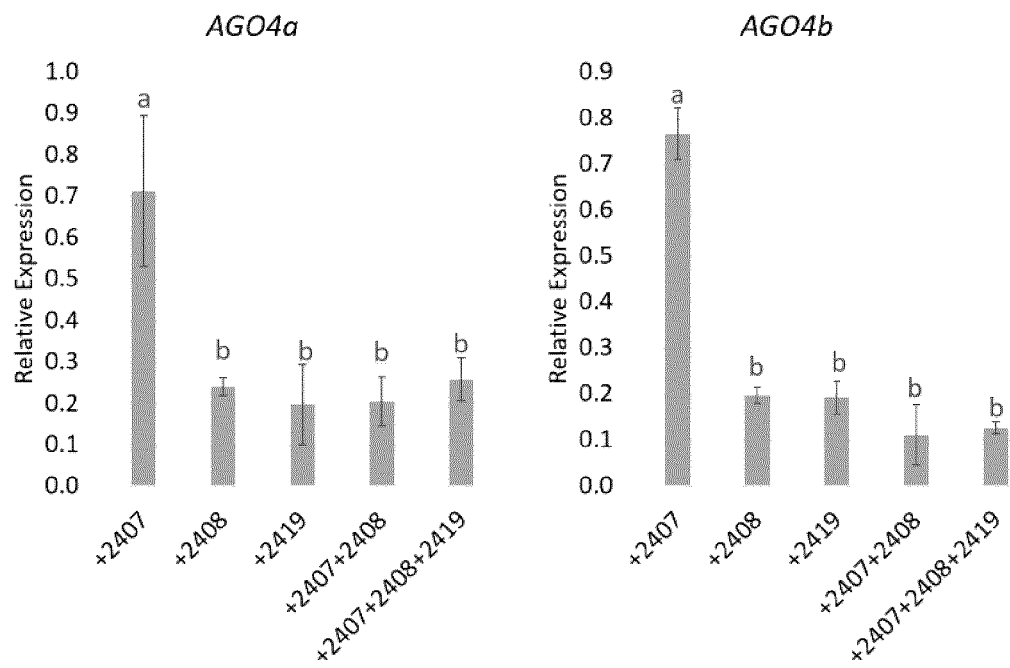
FIG. 17 shows expression of NbAGO4a and NbAGO4b in Nicotiana benthamiana KDFX in response to infiltration with Agrobacterium AT564 containing various T-DNA vectors. Subset of treatments from FIG. 15. See FIG. 15 caption for more details.

As shown in FIGS. 16 and 17, individually or in combination, pPFC2408 and PPFC2419 reduced transcription of AGO4a and AGO4b by about 80% and up to 90% when used in combination with pPFC2407.

Figure 18:
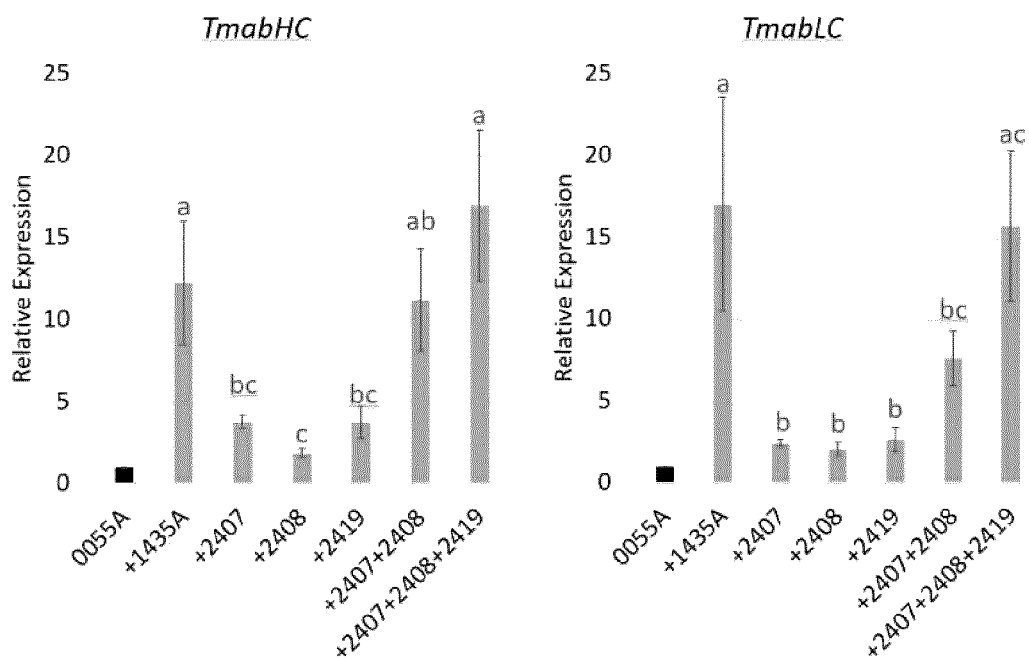
FIG. 18 shows expression of trastuzumab heavy chain (TmabHC) and trastuzumab light chain (TmabLC) in Nicotiana benthamiana KDFX in response to infiltration with Agrobacterium AT564 containing various T-DNA vectors. Treatments were: buffer only pPFC0055A only, pPFC0055A+pPFC1435A (P19), pPFC0055A+pPFC2407 (AGO1-RNAi1), pPFC0055A+pPFC2408 (AGO4-RNAi1), pPFC0055A+pPFC2419 (AGO4-RNAi3), pPFC0055A+pPFC2407+pPFC2408, and pPFC0055A+pPFC2407+pPFC2408+pPFC2419. Total RNA extracted from age-matched leaves from three biological replicates. Two technical replicates performed. Mean±SD. One-way ANOVA, Tukey-post hoc (TmabHC p=0.0001; TmabLC p=0.0002). Relative expression determined by ΔΔCt method (Pfaffl 2001). pPFC0055 only control set as R=1. L23 (ribosomal 60S) used as reference gene (Liu et al 2012).

Expression of trastuzumab heavy chain (TmabHC) and light chain (TmabLC) genes was significantly increase by combined suppression of AGO1- and AGO4 (FIG. 18)

Tmab expression data was consistent with Tmab protein data demonstrating that the combined effect of pPFC2407+pPFC2408+pPFC2419 is greater than the effect of any one of these treatments individually.

Example 4

Methylation of CaMV35S Promoter and 5'-end of Trastuzumab Heavy Chain Coding Sequence in *Nicotiana benthamiana* 7 Days Post-Infiltration DNA methylation is associated with the suppression of gene expression. Plants methylate cytosine in CG, CHG and CHH contexts (H=A, T, or C) (Zhang et al, 2018). De novo DNA methylation in plants is directed by siRNAs through the RNA-directed DNA methylation pathway, in which ARGONAUTE4 (AGO4) is known to play a role (Zhang et al, 2018).

As shown in Examples 1-3, knockdown of AGO1 improved recombinant protein expression compared to the unsuppressed silencing control, but did not achieve yields comparable to the p19 control. In contrast, AGO4 knockdown did not improve yields compared to the unsuppressed silencing control. Significantly, a combination of AGO1 and AGO4 knockdown achieved yields comparable to that of the p19 control.

Figure 19:
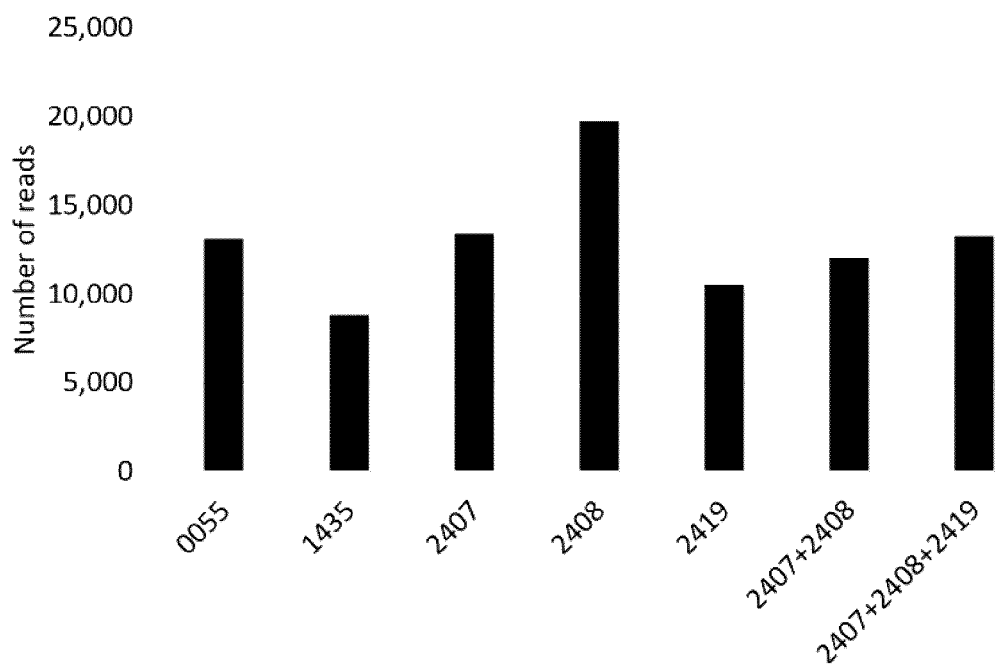
FIG. 19 shows the methylation status of a 423 bp region of the CaMV35S promoter and the 5' end of the trastuzumab heavy chain coding sequence at 7 days post-infiltration. The figure shows the number of reads analyzed for each treatment. Genomic DNA was extracted from age-matched leaves from a single biological replicate. Pair-end reads were trimmed for quality and length and then merged.

Sodium bisulfite treatment and Illumine Mi-Seq sequencing were performed to examine the methylation status of a 423 bp region of the CaMV35S promoter and the 5'-end of the trastuzumab heavy chain coding sequence at 7 days post-infiltration. Between 8837 and 19,713 high quality reads were generated for each sample (FIG. 19).

Figure 20:
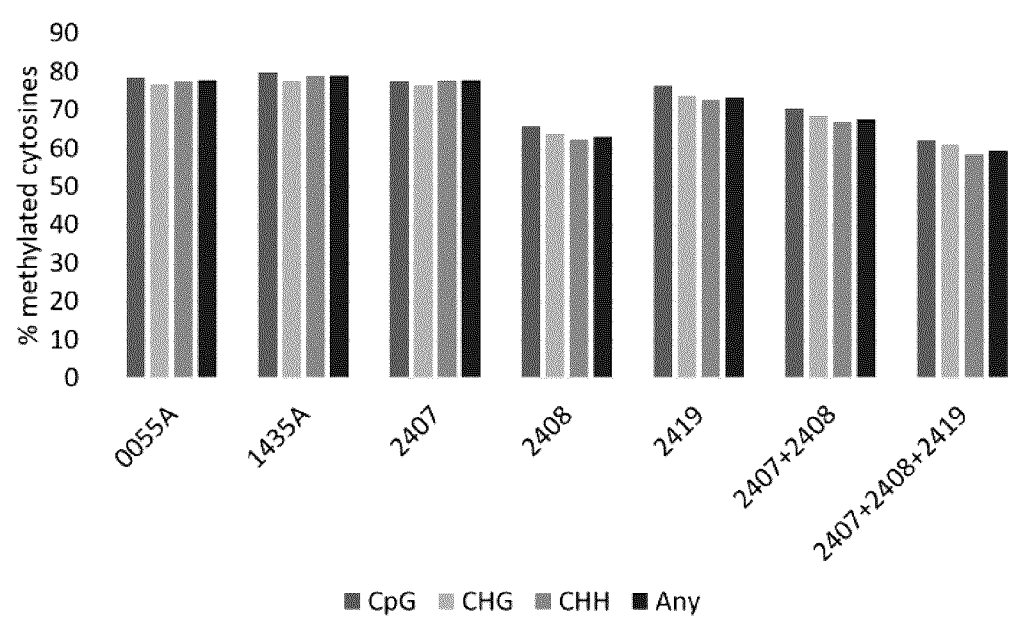
FIG. 20 shows the percentage of methylated cytosines in a 423 bp region of the CaMV35S promoter and 5'-end of trastuzumab heavy chain coding sequence. From left to right, the bars represent CpG, CHG, CHH and Any.

In the unsuppressed silencing control ("0055"), the p19 control ("1435"), and the AGO1 knockdown treatment ("2407"), cytosines in the target region displayed 77-80% methylation (FIG. 20). Knockdown of AGO4 ("2408" and "2419" treatments) reduced methylation by 5-20% in all sequence contexts depending on the treatment combination (FIG. 20).

These results provide a mechanistic explanation for the effect of AGO4 knockdown when combined with AGO1 knockdown. This also differentiates an AGO1+AGO4 knockdown approach from the conventional method of co-expression of p19 since the latter had no effect on the status of cytosine methylation in the examined T-DNA region (FIG. 20).

Methods for Example 4

Genomic DNA Extraction

Genomic DNA was extracted from age-matched leaves (same source material as used for total RNA extraction) using a DNeasy Plant Mini Kit (Qiagen) as per the manufacturer's instructions. Genomic DNA concentration was estimated using a NanoDrop 2000c (ThermoScientific) and integrity confirmed by gel electrophoresis. DNA was stained with EZ-Vision® Two (Amresco, Cat. N650). 1% agarose gels were visualized on a Gel-Doc Universal Hood II (Quantity One software v 4.6.7, Bio-Rad).

Sodium Bisulfite Treatment and Target Region Amplification

Sodium bisulfite conversion of unmethylated cytosines was performed using an EpiTect Bisulfite Kit (Qiagen). The manufacturer's low concentration protocol was used to convert 450 ng of genomic DNA from each sample.

A 423 bp region spanning the 3'-end of the CaMV35S promoter and 5'-end of trastuzumab heavy chain coding sequence was amplified using 0.2 µM of primers 9 and 10 (SEQ ID 18 and 19, respectively) and EpiMark Hot Start Taq Polymerase (New England Biolabs). PCR program: 1) 95° C. 30 sec, 2) 95° C. 15 sec, 60° C. 30 sec, 68° C. 1 min (step 2 run for 5 cycles), 3) 95° C. 15 sec, 68° C. 30 sec (step 3 run for 30 cycles), 4) 68° C. 5 min.

Paired End Sequencing and Methylation Analysis

Illumine MiSeq library preparation was performed as per the 16S Metagenomic Sequencing Library Preparation protocol (Illumina). Analysis was conducted using CLC Genomics Workbench v 11.0 (Qiagen) and the Bisulfite Sequencing Plugin.

TABLE 5

Bisulfite sequencing target

| Primer number | Primer Name | SEQ ID # | Sequence (5'->3') |
|---|---|---|---|
| 9 | KF-ILM-35S-BS-F | 18 | TCGTCGGCAGCGTCA-GATGTGTATAAG AGACAGATYAAAAGGAY-AGTAGAAAAG GAAGGTGG |
| 10 | KF-ILM-TmabHC-BS-R | 19 | GTCTCGTGGGCTCG-GAGATGTGTATAA GAGACAGAACTAARCCACCTC-CACTCT CAACAA |

REFERENCES

Almquist, K. C., Y. Niu, M. D. McLean, F. L. Mena, K. Y. Yau et al., 2004 Immunomodulation confers herbicide resistance in plants. Plant Biotechnology Journal 2: 189-197. Altschul, S. F., W. Gish, W. Miller, E. W. Myers and D. J. Lipman, 1990 Basic local alignment search tool. J Mol Biol 215: 403-410.

Almquist, K. C., M. D. McLean, Y. Niu, G. Byrne, F. C. Olea-Popelka et al., 2006 Expression of an anti-botulinum toxin A neutralizing single-chain Fv recombinant antibody in transgenic tobacco. Vaccine 24: 2079-208.

An, Y. Q., McDowell, J. M., Huang, S., McKinney, E. C., Chambliss, S., & Meagher, R. B. (1996). Strong, constitutive expression of the *Arabidopsis* ACT2/ACT8 actin subclass in vegetative tissues. *The Plant Journal,* 10(1), 107-121.

An, Y. Q. C., & Meagher, R. B. (2010). Strong expression and conserved regulation of ACT2 in *Arabidopsis thaliana* and Physcomitrella patens. *Plant molecular biology reporter,* 28(3), 481-490.

Angel, C. A., Hsieh, Y. C., & Schoelz, J. E. (2011). Comparative analysis of the capacity of tombusvirus P22 and P19 proteins to function as avirulence determinants in *Nicotiana* species. *Molecular plant-microbe interactions,* 24(1), 91-99.

Bardor, M., C. Faveeuw, A. C. Fitchette, D. Gilbert, L. Galas et al., 2003 Immunoreactivity in mammals of two typical plant glyco-epitopes, core alpha(1,3)-fucose and core xylose. Glycobiology 13: 427-434.

Bradford M. M. (1976) A rapid and sensitive method for the quantitation of microgram quantities of protein utilizing the principle of protein-dye binding. *Anal Biochem,* 72, 248-254.

Brodsky, L. I.; Ivanov, V. V.; Kalaidzidis, Y. L.; Leontovich, A. M.; Nikolaev, V. K.; Feranchuk, S. I.; Drachev, V. A. GeneBee-NET: internet-based server for analyzing biopolymers structures. Biochemestry 1995, 60, 923-928.

Broothaerts, W., H. J. Mitchell, B. Weir, S. Kaines, L. M. Smith et al., 2005 Gene transfer to plants by diverse species of bacteria. Nature 433: 629-633.

Choi, B.-K., Warburton, S., Lin, H., Patel, R., Boldogh, I., Meehl, M., d'Anjou, M., Pon, L., Stadheim, T. A., and Sethuraman, N., 2012. Improvement of N-glycan site occupancy of therapeutic glycoproteins produced in *Pichia pastoris*. Appl. Microbiol. Biotechnol. 95:671-682.

Chung, S. M., M. Vaidya and T. Tzfira, 2006 *Agrobacterium* is not alone: gene transfer to plants by viruses and other bacteria. Trends Plant Sci 11: 1-4.

Colgan, R., C. J. Atkinson, M. Paul, S. Hassan, P. M. Drake et al., 2010 Optimisation of contained *Nicotiana tabacum* cultivation for the production of recombinant protein pharmaceuticals. Transgenic Res 19: 241-256.

Conley, A. J., Zhu, H., Le, L. C., Jevnikar, A. M., Lee, B. H., Brandle, J. E. and Menassa, R. (2011) Recombinant protein production in a variety of *Nicotiana* hosts: a comparative analysis. Plant Biotechnol J. 9, 434-444.

Cox, K. M., J. D. Sterling, J. T. Regan, J. R. Gasdaska, K. K. Frantz et al., 2006 Glycan optimization of a human monoclonal antibody in the aquatic plant *Lemna minor*. Nature Biotechnology 24: 1591-1597.

Garabagi, F., Gilbert, E., Loos, A., McLean, M. D., & Hall, J. C. (2012). Utility of the P19 suppressor of gene-silencing protein for production of therapeutic antibodies in *Nicotiana* expression hosts. *Plant biotechnology journal,* 10(9), 1118-1128.

Galvin, S. B., 2003 *Agrobacterium*-mediated plant transformation: the biology behind the "gene-jockeying" tool. Microbiology and Molecular Biology Reviews 67: 16-37.

Giritch, A., S. Marillonnet, C. Engler, G. van Eldik, J. Botterman et al., 2006 Rapid high-yield expression of full-size IgG antibodies in plants coinfected with non-competing viral vectors. Proceedings of the National Academy of Sciences USA 103: 14701-14.

Horsch, R. B., S. G. Rogers and R. T. Fraley, 1985 Transgenic plants. Cold Spring Harb Symp Quant Biol 50: 433-437.

Jin, C., F. Altmann, R. Strasser, L. Mach, M. Schahs et al., 2008 A plant-derived human monoclonal antibody induces an anti-carbohydrate immune response in rabbits. Glycobiology 18: 235-241.

Jones, L., Keining, T., Eamens, A., & Vaistij, F. E. (2006). Virus-induced gene silencing of argonaute genes in *Nicotiana benthamiana* demonstrates that extensive systemic silencing requires Argonaute1-like and Argonaute4-like genes. *Plant physiology,* 141(2), 598-606.

Karlin, S., and S. F. Altschul, 1990 Methods for assessing the statistical significance of molecular sequence features by using general scoring schemes. Proc Natl Acad Sci USA 87: 2264-2268.

Kozak, M., 1984 Compilation and analysis of sequences upstream from the translational start site in eukaryotic mRNAs. Nucleic Acids Res 12: 857-872.

Li, Q.; Hunt, A. A near-stream element in a plant polyadenylation signal consist of more than six nucleotides. Plant Mol. Biol. 1995, 28, 927-934.

Liu, D., Shi, L., Han, C., Yu, J., Li, D., & Zhang, Y. (2012). Validation of reference genes for gene expression studies in virus-infected *Nicotiana benthamiana* using quantitative real-time PCR. *PLoS One,* 7(9), e46451.

Makvandi-Nejad, S., M. D. McLean, T. Hirama, K. C. Almquist, C. R. Mackenzie et al., 2005 Transgenic tobacco plants expressing a dimeric single-chain variable fragment (scfv) antibody against *Salmonella enterica* serotype Paratyphi B. Transgenic Res 14: 785-792.

Marillonnet, S., C. Thoeringer, R. Kandzia, V. Klimyuk and Y. Gleba, 2005 Systemic *Agrobacterium tumefaciens*-mediated transfection of viral replicons for efficient transient expression in plants. Nature Biotechnology 23: 718-723.

McLean, M. D., K. C. Almquist, Y. Niu, R. Kimmel, Z. Lai et al., 2007 A human anti-*Pseudomonas aeruginosa* serotype O6ad immunoglobulin G1 expressed in transgenic tobacco is capable of recruiting immune system effector function in vitro. Antimicrobial Agents and Chemotherapy 51: 3322-332.

Myers, E. W., and W. Miller, 1988 Optimal alignments in linear space. Comput Appl Biosci 4: 11-17.

Odokonyero, D., Mendoza, M. R., Moffett, P., & Scholthof, H. B. (2017). Tobacco rattle virus (TRV)-Mediated Silencing of *Nicotiana benthamiana* ARGONAUTES (NbAGOs) Reveals New Antiviral Candidates and Dominant Effects of TRV-NbAGO1. Phytopathology, 107(8), 977-987.

Ohme-Takagi, M.; Taylor, C.; Newman, T.; Green, P. The effect of sequences with high AU content on mRNA stability in tobacco. Proc. Natl. Acad. Sci. U.S.A. 1993, 90, 11811-11815.

Olea-Popelka, F., M. D. McLean, J. Horsman, K. Almquist, J. E. Brandle et al., 2005 Increasing expression of an anti-picloram single-chain variable fragment (ScFv) antibody and resistance to picloram in transgenic tobacco (*Nicotiana tabacum*). Journal of Agricultural and Food Chemistry 53: 6683-6690.

Pfaffl, M. W. (2001). A new mathematical model for relative quantification in real-time RT-PCR. Nucleic acids research, 29(9), e45-e45.

Rademacher, T., Sack, M., Arcalis, E., Stadlmann, J., Balzer, S., Altmann, F., Quendler, H., Stiegler, G., Kunert, R., Fischer, R. and Stoger, E. (2008). Recombinant antibody 2G12 produced in maize endosperm efficiently neutralizes HIV-1 and contains predominantly single-GlcNAc N-glycans. *Plant biotechnology journal,* 6(2), 189-201.

Rothnie, H. M. Plant mRNA 3'-end formation. Plant Mol. Biol. 1996, 32, 43-61.

Samac, D. A., C. M. Hironaka, P. E. Yallaly and D. M. Shah, 1990 Isolation and Characterization of the Genes Encoding Basic and Acidic Chitinase in *Arabidopsis thaliana*. Plant Physiol 93: 907-914.

Scholthof, H. B., Alvarado, V. Y., Vega-Arreguin, J. C., Ciomperlik, J., Odokonyero, D., Brosseau, C., Jaubert, M., Zamora, A., & Moffett, P. (2011). Identification of an ARGONAUTE for antiviral RNA silencing in *Nicotiana benthamiana*. *Plant physiology*, 156(3), 1548-1555.

Shapiro, M. B.; Senapathy, P. RNA splice junctions of different classes of eukaryotes: sequence statistics and functional implications in gene expression. Nucleic Acids Res. 1987, 5, 7155-7174.

Sourrouille, C., E. Marquet-Blouin, M. A. D'Aoust, M. C. Kiefer-Meyer, M. Seveno et al., 2008 Down-regulated expression of plant-specific glycoepitopes in alfalfa. Plant Biotechnology Journal 6: 702-721.

Strasser, R., Stadlmann, J., Schähs, M., Stiegler, G., Quendler, H., Mach, L., Glössl, J., Weterings, K., Pabst, M. and Steinkellner, H. (2008). Generation of glyco-engineered *Nicotiana benthamiana* for the production of monoclonal antibodies with a homogeneous human-like N-glycan structure. Plant biotechnology journal, 6(4), 392-402.

Vamvaka, E., Twyman, R. M., Murad, A. M., Melnik, S., Teh, A. Y. H., Arcalis, E., Altmann, F., Stoger, E., Rech, E., Ma, J. K. and Christou, P., (2016). Rice endosperm produces an underglycosylated and potent form of the HIV-neutralizing monoclonal antibody 2G12. *Plant biotechnology journal*, 14(1), 97-108.

Yu, D., M. D. McLean, J. C. Hall and R. Ghosh, 2008 Purification of a human immunoglobulin G1 monoclonal antibody from transgenic tobacco using membrane chromatographic processes. J Chromatogr A 1187: 128-137.

Yu, D., M. D. McLean, J. C. Hall and R. Ghosh, 2008 Purification of a monoclonal antibody from tobacco extract using membrane-based bioseparation techniques. J Membr Sci 323: 159-166.

Zhang, H., Lang, Z., & Zhu, J. K. (2018). Dynamics and function of DNA methylation in plants. *Nature Reviews Molecular Cell Biology*, 1.

The invention claimed is:

1. A plant or plant cell with reduced endogenous AGO1 and AGO4 expression compared to a wild-type plant or plant cell, wherein the plant or plant cell expresses at least two short hairpin RNA (shRNA), wherein a first shRNA targets AGO1 and a second shRNA targets AGO4 and wherein the plant or plant cell comprises a nucleic acid sequence encoding a recombinant protein.

2. The plant or plant cell of claim 1, wherein the first shRNA comprises
   (a) a nucleic acid molecule comprising SEQ ID NO: 5 or a fragment thereof, a sequence having at least 75%, 80%, 85%, 90%, 95% or 99% sequence identity to SEQ ID NO: 5 or a fragment thereof; or the complement thereof, and/or
   wherein the second shRNA comprises
   (a) a nucleic acid molecule comprising SEQ ID NO: 6 or a fragment thereof, a sequence having at least 75%, 80%, 85%, 90%, 95% or 99% sequence identity to SEQ ID NO: 6 or a fragment thereof; or the complement thereof, or
   (b) a nucleic acid molecule comprising SEQ ID NO: 7 or a fragment thereof, a sequence having at least 75%, 80%, 85%, 90%, 95% or 99% sequence identity to SEQ ID NO: 7 or a fragment thereof; or the complement thereof.

3. The plant or plant cell of claim 2, wherein the first shRNA comprises a nucleic acid molecule comprising SEQ ID NO: 5 or a fragment thereof, a sequence having at least 75%, 80%, 85%, 90%, 95% or 99% sequence identity to SEQ ID NO: 5 or a fragment thereof; or the complement thereof,
   the second shRNA comprises a nucleic acid molecule comprising SEQ ID NO: 6 or a fragment thereof, a sequence having at least 75%, 80%, 85%, 90%, 95% or 99% sequence identity to SEQ ID NO: 6 or a fragment thereof; or the complement thereof,
   and the plant or plant cell further expresses a third shRNA, wherein the third shRNA comprises a nucleic acid molecule comprising SEQ ID NO: 7 or a fragment thereof, a sequence having at least 75%, 80%, 85%, 90%, 95% or 99% sequence identity to SEQ ID NO: 7 or a fragment thereof; or the complement thereof.

4. The plant or plant cell of claim 1, wherein multiple AGO1 and/or AGO4 genes have reduced endogenous expression compared to a wild-type plant or plant cell.

5. The plant or plant cell of claim 1, wherein the plant or plant cell is a tobacco plant or plant cell, optionally a *Nicotiana* plant or plant cell.

6. The plant or plant cell of claim 5, wherein the plant or plant cell is a *Nicotiana* plant or plant cell and has reduced endogenous AGO1-1 and AGO1-2 expression compared to a wild-type plant or plant cell, and/or has reduced endogenous AGO4-1 and AGO4-2 expression compared to a wild-type plant or plant cell.

7. The plant or plant cell of claim 1, wherein the plant or plant cell further expresses a nucleic acid molecule encoding the P19 protein from Tomato Bushy Stunt Virus (TBSV).

8. The plant or plant cell of claim 1, wherein the plant or plant cell expresses a nucleic acid molecule encoding the STT3D protein from *Leishmania*, optionally wherein the expression of the nucleic acid molecule encoding the STT3D protein is driven by the 35S or AtACT2 promoter.

9. The plant or plant cell of claim 1, wherein the plant or plant cell has increased expression of the recombinant protein compared to a wild-type plant or plant cell comprising the nucleic acid sequence.

10. The plant or plant cell of claim 1, wherein the recombinant protein is an antibody or fragment thereof, a therapeutic enzyme or a vaccine or a Virus Like Particle.

11. A method of enhancing the production of a recombinant protein in a plant or plant cell comprising:
   (a) introducing and expressing the nucleic acid molecule encoding the recombinant protein in the plant or plant cell of claim 1; and
   (b) growing the plant or plant cell to obtain a plant or plant cell that expresses the recombinant protein.

* * * * *

SEQUENCE LISTING

<160> NUMBER OF SEQ ID NOS: 19

<210> SEQ ID NO 1
<211> LENGTH: 21
<212> TYPE: PRT
<213> ORGANISM: Arabidopsis thaliana

<400> SEQUENCE: 1

```
Met Ala Lys Thr Asn Leu Phe Leu Phe Leu Ile Phe Ser Leu Leu Leu
1               5                   10                  15

Ser Leu Ser Ser Ala
            20
```

<210> SEQ ID NO 2
<211> LENGTH: 28
<212> TYPE: PRT
<213> ORGANISM: Homo sapiens

<400> SEQUENCE: 2

```
Met His Ser Lys Val Thr Ile Ile Cys Ile Arg Phe Leu Phe Trp Phe
1               5                   10                  15

Leu Leu Leu Cys Met Leu Ile Gly Lys Ser His Thr
            20                  25
```

<210> SEQ ID NO 3
<211> LENGTH: 2571
<212> TYPE: DNA
<213> ORGANISM: Leishmania major

<400> SEQUENCE: 3

```
atgggtaagc gtaagggcaa cagccttggt gattctggtt ctgctgctac cgcttctaga      60
gaggcttctg ctcaagctga agatgctgct tctcagacca agactgctag ccctcctgct     120
aaggttatcc tgcttcctaa gaccttgacc gacgagaagg actttatcgg gatcttccct     180
tttccgttct ggcctgtgca tttcgtgctt actgttgtgg ctcttttcgt gctggctgct     240
tcttgctttc aggctttcac cgtgaggatg atcagcgtgc agatctacgg ttacctgatc     300
cacgagttcg acccgtggtt taattacagg gctgccgagt acatgtctac ccatggttgg     360
tctgctttct tcagctggtt cgactacatg agctggtatc ctcttggtag gcctgtgggt     420
```

-continued

```
tctactactt atcctggact tcagcttacc gctgtggcta ttcatagagc tttggctgct    480
gctggcatgc cgatgtctct aacaatgtg tgcgtgctga tgcctgcatg gttcggtgct    540
attgctactg ctactttggc cttctgtacc tacgaggctt caggttctac tgttgctgct   600
gcagctgctc tctgagcttc tctattatt cctgctcacc tgatgcggag catggctggt   660
gaatttgaca acgagtgcat tgctgtggct gctatgcttc tgactttcta ctgctgggtg   720
agatcccttta ggaccagatc ttcttggcct attggtgtgc ttaccggtgt tgcttacggt  780
tacatggctg cagcttgggg cggttacatt ttcgtgttga acatggtggc tatgcacgcc   840
ggcattagct ctatggttga ttgggctcgt aatacttaca acccgagcct tcttagggct   900
tacacccttt tctacgtggt gggaaccgct attgctgttt gtgttcctcc tgtgggcatg   960
agcccttttca gtctcttga acagcttggt gctctgctgg tgcttgtttt cttgtgcgga   1020
cttcaggttt gcgaggtgtt gagagctaga gctggtgttg aggttaggtc cagggctaac   1080
ttcaagatca gagtgagggt gttctccgtt atggctggcg ttgcagctct tgctatttct   1140
gtgcttgctc ctaccggtta cttcggtcct ttgtctgtta gggtgagagc cttgttcgtt   1200
gagcatacca ggactggtaa ccctctggtt gattctgttg ctgagcatca gcctgcttct   1260
ccagaggcta tgtgggcttt tcttcatgtg tgcggtgtga cttggggtct gggttctatt   1320
gtgttggctg tgtctacctt cgtgcactac agcccttcta aggtgttctg gcttctgaac   1380
tctggcgccg tgtactactt ctctactagg atggctaggc cctgcttct ttctggacct    1440
gctgcttgtc ttagcaccgg tattttcgtg ggcaccattc ttgaagctgc cgtgcagttg   1500
tctttctggg attctgatgc taccaaggcc aaaaagcagc aaaagcaggc tcagaggcat   1560
cagagaggtg ctggtaaagg ttctggtagg gatgacgcta agaatgctac taccgctcgg   1620
gctttctgtg atgtgtttgc tggttcttct ctggcttggg gtcaccgtat ggtgctttct   1680
attgcaatgt gggctcttgt gactaccacc gccgtttctt tcttctcctc cgaattcgct   1740
tcccacagca ctaagttcgc tgagcagtca agcaacccga tgattgtgtt cgctgctgtt   1800
gtgcagaatc gtgctactgg caagcctatg aacctgctgg tggatgatta cctgaaggct   1860
tacgagtggc tgagggattc tactcctgag gatgctagag ttctcgcttg gtgggattac   1920
ggctaccaga ttaccggtat tggcaacagg acctctctgg ctgatggtaa tacttggaac   1980
cacgagcaca ttgccaccat cggtaagatg cttactagcc ctgttgtcga ggctcactct   2040
cttgttaggc acatggctga ttacgtgctg atttgggctg gtcagtctgg cgatcttatg   2100
aagtctcctc acatggctag gatcggcaac tctgtgtacc acgatatctg ccctgatgat   2160
cctctttgcc agcagttcgg tttccaccgg aatgattact ctcggcctac tcctatgatg   2220
cgggcttctc ttctttacaa ccttcacgag gctggtaagc ggaaaggtgt taaggtgaac   2280
ccgagcttgt tccaagaggt gtacagctct aagtacggcc tggtgaggat cttcaaggtg   2340
atgaatgtga cgcccgagag caagaagtgg gttgcagatc ctgctaatag ggtgtgccat   2400
cctcctggtt cttggatttg tcctggtcag taccctccgg ccaaagaaat tcaagagatg   2460
ctggctcata gggtgccgtt cgatcaggtt accaacgctg atcggaagaa caacgtgggg   2520
tcttatcaag aggagtacat gcggaggatg cgtgagtctg agaatagaag g            2571
```

<210> SEQ ID NO 4
<211> LENGTH: 519
<212> TYPE: DNA
<213> ORGANISM: Artificial Sequence
<220> FEATURE:
<223> OTHER INFORMATION: Synthetic construct

<400> SEQUENCE: 4

```
atggaaaggg ctattcaggg aaatgatgct agagagcagg ctaattctga aagatgggat    60
ggtggatctg gtggaactac ttctccattc aagcttccag atgagtctcc atcttggact   120
gagtggaggc ttcataacga tgagactaac tccaatcagg ataacccact cggattcaaa   180
gaatcttggg gattcggaaa ggttgtgttc aagcgttacc ttaggtatga taggactgag   240
gcttcacttc atagggttct cggatcttgg actggtgatt ctgttaacta cgctgcttct   300
cgttttcttg gattcgatca gatcggatgc acttactcta ttaggttcag gggagtgtct   360
attactgttt ctggtggatc taggactctt caacaccttt gcgagatggc tattaggtct   420
aagcaagagc ttcttcagct tgctccaatt gaggttgagt ctaacgtttc aagaggatgt   480
ccagaaggta ctgagacttt cgagaaagaa tccgagtga                          519
```

<210> SEQ ID NO 5
<211> LENGTH: 849
<212> TYPE: DNA
<213> ORGANISM: Nicotiana benthamiana

<400> SEQUENCE: 5

```
gagtcgtctc acagtgctgt ttgacaaaac atgtatttaa gatgagcaaa cagtatctag    60
ccaatgtagc gctgaaaatc aatgtgaagg tgggagggag aaacactgtg cttgttgatg   120
caatatcgag gcgaattcct cttgtcagcg accggcctac catcattttt ggtgcagatg   180
tcacccaccc tcaccctggg gaggactcta gcccatccat tgccgcggtg gttgcttctc   240
aagattggcc tgagattaca agtatgctg gtctagtttc tgctcaagcc ataggcaag    300
agcttattca ggatctgtac acgactaggc aagatcctgt taaggggaca gttgctggtg   360
gaatgattaa ggacttactt atatccttcc gaagagctac tggacaaaag ccccagagaa   420
taattttcta tagggatggt gttagtgaag acaattttta tcaagtgctt ctgttcgaac   480
ttgatgcgat ccgcaaagca tgtgcgtctt tggagccaaa ttatcagccc ccagtcacat   540
ttgttgtggt tcagaaacga catcacacaa ggcttttttgc caataaccac cgtgacagaa   600
atgcagttga caggagcggg aacattatac ctggtactgt tgtagattca aagatatgcc   660
acccgacaga gtttgatttc tatctttgta gccatgccgg catacagggt acgagccgtc   720
cagctcacta ccatgttcta tgggacgaga acaaattcac agccgatgcg ctgcagtctt   780
tgaccaacaa cctctgctat acatatgcaa ggtgcacgcg ttccgtctcc atcgttcccc   840
ctgcatatt                                                          849
```

<210> SEQ ID NO 6
<211> LENGTH: 380
<212> TYPE: DNA
<213> ORGANISM: Nicotiana benthamiana

<400> SEQUENCE: 6

```
caggagagga tgcaagtcct aagcaatgcc ctcaaaatca acaaatatga tgccgagcct    60
ctgcttcgtg cctgtggaat ttcaatcagc agtaacttca cccaggttga agggcgtgtt   120
ctttctcccc caaagttgaa gacaggtggt gatgactttg ttccccgtaa tggcaggtgg   180
aatttcaata caagagact ggtcgatcct accaagatag agcgttgggc tgttgtcaac   240
ttttctgcac gttgtaacat acaagggcta atcagtgatc ttataaaatg tgggaaaatg   300
aaaggaatta tggtggaaga tccatttgat gttttttgaag agtctccaca attcagaagg   360
```
gctccgccac ttgtcagagt                                                  380

<210> SEQ ID NO 7
<211> LENGTH: 260
<212> TYPE: DNA
<213> ORGANISM: Nicotiana benthamiana

<400> SEQUENCE: 7
gagcttcagt gcgcacccag tctcctaaag tggagatgat agacaacttg tttaaacgtg    60
cttctgacac tgaggatgag gggataatga gggaggcttt gctagatttt tatgtgagtt   120
ctggaaaaag gaagcctgag catattatta tattcaggga tggtgtcagt gaatctcaat   180
ttaatcaagt tctgaacatt gaactggatc agatcattga ggcgtgtaaa tttctcgacg   240
agaagtggtc accaaagttt                                                260

<210> SEQ ID NO 8
<211> LENGTH: 210
<212> TYPE: DNA
<213> ORGANISM: Arabidopsis thaliana

<400> SEQUENCE: 8
cactgcacgg tatgctcctc ttcttgttca tggtcatgat ccttatatga gcagggaaag    60
tccagtttag acttgtagtt agttactctt cgttatagga tttggatttc ttgcgtgttt   120
atggttttag tttccctcct tgatgaata aaattgaatc ttgtatgagt ttcatatcca   180
tgttgtgaat cttttgcag acgcagctag                                     210

<210> SEQ ID NO 9
<211> LENGTH: 1168
<212> TYPE: DNA
<213> ORGANISM: Arabidopsis thaliana

<400> SEQUENCE: 9
tgattcagaa tcgttttgac gagttcggat gtagtagtag ccattattta atgtacatac    60
taatcgtgaa tagtgaatat gatgaaacat tgtatcttat tgtataaata tccataaaca   120
catcatgaaa gacactttct ttcacggtct gaattaatta tgatacaatt ctaatagaaa   180
acgaattaaa ttacgttgaa ttgtatgaaa tctaattgaa caagccaacc acgacgacga   240
ctaacgttgc ctggattgac tcggtttaag ttaaccacta aaaaaacgga gctgtcatgt   300
aacacgcgga tcgagcaggt cacagtcatg aagccatcaa agcaaagaa ctaatccaag    360
ggctgagatg attaattagt ttaaaaatta gttaacacga gggaaaaggc tgtctgacag   420
ccaggtcacg ttatctttac ctgtggtcga atgattcgt gtctgtcgat tttaattatt    480
tttttgaaag gccgaaaata aagttgtaag agataaaccc gcctatataa attcatatat   540
tttcctctcc gctttgaatt gtctcgttgt cctcctcact ttcatcagcc gttttgaatc   600
tccggcgact tgacagagaa gaacaaggaa gaagactaag agagaaagta agagataatc   660
caggagattc attctccgtt ttgaatcttc ctcaatctca tcttcttccg ctctttcttt   720
ccaaggtaat aggaactttc tggatctact ttatttgctg gatctcgatc ttgttttctc   780
aatttccttg agatctggaa ttcgtttaat ttggatctgt gaacctccac taaatctttt   840
ggttttacta gaatcgatct aagttgaccg atcagttagc tcgattatag ctaccagaat   900
ttggcttgac cttgatggag agatccatgt tcatgttacc tgggaaatga tttgtatatg   960
tgaattgaaa tctgaactgt tgaagttaga ttgaatctga acactgtcaa tgttagattg  1020
aatctgaaca ctgtttaagg ttagatgaag tttgtgtata gattcttcga aactttagga  1080
tttgtagtgt cgtacgttga acagaaagct atttctgatt caatcagggt ttatttgact    1140
gtattgaact cttttgtgt gtttgcag                                        1168

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
cgaaccaacg acacagcaag                                                  20

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
gctggctcac gaagtcaata                                                  20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
gctgcaatga ctactcagcc                                                  20

<210> SEQ ID NO 13
<211> LENGTH: 21
<212> TYPE: DNA
<213> ORGANISM: Artificial Sequence
<220> FEATURE:
<223> OTHER INFORMATION: Synthetic construct

<400> SEQUENCE: 13
gtctagatgg cacatctcgg t                                                21

<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
cctggcaaac atggaagtcc                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
ttgctactga ttgagacgcc                                                  20

<210> SEQ ID NO 16

```
<211> LENGTH: 21
<212> TYPE: DNA
<213> ORGANISM: Artificial Sequence
<220> FEATURE:
<223> OTHER INFORMATION: Synthetic construct

<400> SEQUENCE: 16
gctttaggac cactcagagt g                                              21

<210> SEQ ID NO 17
<211> LENGTH: 20
<212> TYPE: DNA
<213> ORGANISM: Artificial Sequence
<220> FEATURE:
<223> OTHER INFORMATION: Synthetic contruct

<400> SEQUENCE: 17
gggcattgct taggacttgc                                                20

<210> SEQ ID NO 18
<211> LENGTH: 62
<212> TYPE: DNA
<213> ORGANISM: Artificial Sequence
<220> FEATURE:
<223> OTHER INFORMATION: Synthetic construct

<400> SEQUENCE: 18
tcgtcggcag cgtcagatgt gtataagaga cagatyaaaa ggayagtaga aaaggaaggt    60
gg                                                                   62

<210> SEQ ID NO 19
<211> LENGTH: 60
<212> TYPE: DNA
<213> ORGANISM: Artificial Sequence
<220> FEATURE:
<223> OTHER INFORMATION: Synthetic construct

<400> SEQUENCE: 19
gtctcgtggg ctcggagatg tgtataagag acagaactaa rccacctcca ctctcaacaa    60
```